(12) United States Patent
Benner

(10) Patent No.: US 6,444,798 B1
(45) Date of Patent: Sep. 3, 2002

(54) CHIMERAS OF SULFUR-LINKED OLIGONUCLEOTIDE ANALOGS AND DNA AND RNA

(76) Inventor: Steven Albert Benner, 1501 NW. 68th Ter., Gainesville, FL (US) 32605

( * ) Notice: Subject to any disclaimer, the term of this patent is extended or adjusted under 35 U.S.C. 154(b) by 0 days.

(21) Appl. No.: 08/645,411

(22) Filed: May 13, 1996

Related U.S. Application Data

(60) Continuation-in-part of application No. 08/068,981, filed on May 28, 1993, now abandoned, which is a division of application No. 07/202,528, filed on Jun. 6, 1988, now Pat. No. 5,216,141.

(51) Int. Cl.[7] ..................... A61K 31/7125; C07H 21/00
(52) U.S. Cl. .................... 536/23.1; 435/6; 435/375; 536/24.3; 536/24.5
(58) Field of Search ................. 435/6, 375; 514/44; 536/23.1, 24.3, 24.5, 25.3

(56) References Cited

U.S. PATENT DOCUMENTS

| | | | | |
|---|---|---|---|---|
| 5,378,825 A | * | 1/1995 | Cook et al. ............... | 536/25.43 |
| 5,432,272 A | * | 6/1995 | Benner ..................... | 536/25.3 |
| 5,216,141 A | * | 7/1995 | Benner .................... | 536/27.13 |

OTHER PUBLICATIONS

Agrawal et al "Modified oligonucleotides as therapeutic and diagnostic agents" Curr. Opinion Biotech. 6: 12–19, 1995.*

Baeschlin et al. "Chimera of dimethylene sulfone–, methyl sulfide–and methyl sulfoxide–linked ribonucleotides and DNA" J. Org. Chem. 61: 7620–7626,1996.*

De Mesmaeker et al. "Antisense oligonucleotides" Acc. Chem. Res. 28: 366–374, Sep. 1995.*

Ghosh et al. "Phosphorothioate–phosphodiester oligonucleotide copolymers: assessment for antisense application" Anti–Cancer Drug Design 8: 15–32, 1993.*

Giles et al. Chimeric oligodeoxunycleotide analogues: enhanced cell uptake of structures which direct ribonuclease H with high specificity Anti–Cancer Drug Design 8: 33–55, 1993.*

* cited by examiner

*Primary Examiner*—Remy Yucel
*Assistant Examiner*—Thomas G. Larson

(57) ABSTRACT

This invention dicloses compositions of matter that are oligonucleotide analogs containing one or more improvements, where the improvement consists of replacing one or more of the phosphodiester linking units (—O—$PO_2^-$—O—) by a dimethylene sulfide (—$CH_2$—S—$CH_2$—), sulfoxide (—$CH_2$—SO—$CH_2$—), or sulfone linking unit (—$CH_2$—$SO_2$—$CH_2$—). This linkage is stable to degradation both by enzymes and by alkaline hydrolysis, contains no stereogenic atoms, and confers improved stability and the ability to fold into tertiary structure upon natural oligonucleotides and their analogs.

1 Claim, 1 Drawing Sheet

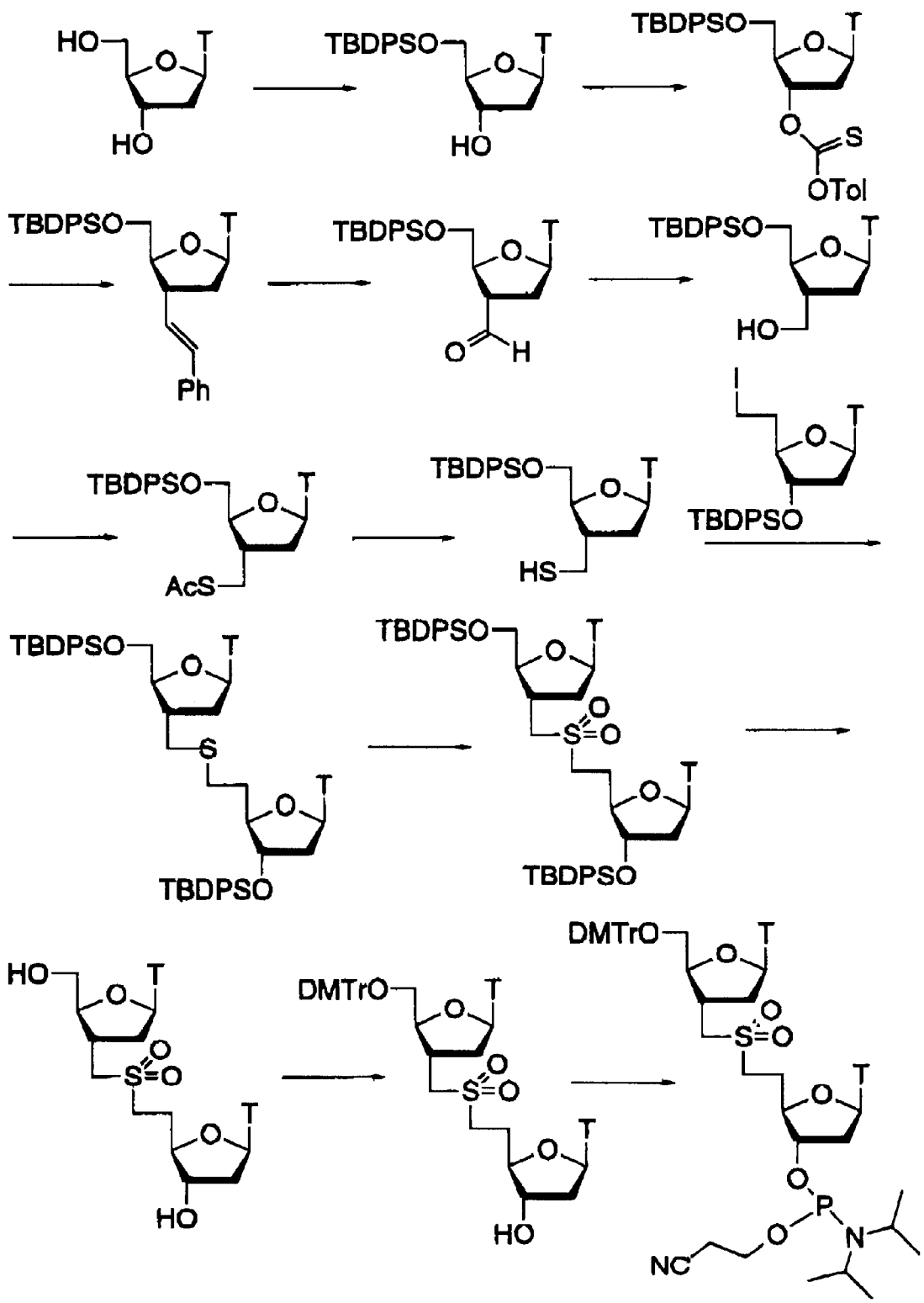

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 16
      (B) TYPE: nucleic acid
      (C) STRANDEDNESS: single
      (D) TOPOLOGY: linear (ii) MOLECULE TYPE: other nucleic acid (vi) ORIGINAL SOURCE:

(xi) SEQUENCE DESCRIPTION: SEQ ID NO: 1:

TTTTTCTAGA TCTGGA                                                16

(2) INFORMATION FOR SEQ ID NO: 2:

(i) SEQUENCE CHARACTERISTICS:
      (A) LENGTH: 16
      (B) TYPE: nucleic acid
      (C) STRANDEDNESS: single
      (D) TOPOLOGY: linear (ii) MOLECULE TYPE: other nucleic acid (vi) ORIGINAL SOURCE:

(xi) SEQUENCE DESCRIPTION: SEQ ID NO: 2:

TCCAGATCTA GAAAAA                                                     16

(2) INFORMATION FOR SEQ ID NO: 3:

(i) SEQUENCE CHARACTERISTICS:
            (A) LENGTH: 10
            (B) TYPE: nucleic acid
            (C) STRANDEDNESS: single
            (D) TOPOLOGY: linear (ii) MOLECULE TYPE: other nucleic acid (vi) ORIGINAL SOURCE:

(xi) SEQUENCE DESCRIPTION: SEQ ID NO: 3:

GCGTTTTGCT                                                            10

(2) INFORMATION FOR SEQ ID NO: 4:

(i) SEQUENCE CHARACTERISTICS:
            (A) LENGTH: 10
            (B) TYPE: nucleic acid
            (C) STRANDEDNESS: single
            (D) TOPOLOGY: linear (ii) MOLECULE TYPE: other nucleic acid (vi) ORIGINAL SOURCE:

(xi) SEQUENCE DESCRIPTION: SEQ ID NO: 4:

AGCAAAACGC                                                            10

(2) INFORMATION FOR SEQ ID NO: 5:

(i) SEQUENCE CHARACTERISTICS:
            (A) LENGTH: 10
            (B) TYPE: nucleic acid
            (C) STRANDEDNESS: single
            (D) TOPOLOGY: linear (ii) MOLECULE TYPE: DNA (vi) ORIGINAL SOURCE:

(xi) SEQUENCE DESCRIPTION: SEQ ID NO: 5:

AGCAAAACGC                                                            10

(2) INFORMATION FOR SEQ ID NO: 6:

(i) SEQUENCE CHARACTERISTICS:
            (A) LENGTH: 16
            (B) TYPE: nucleic acid
            (C) STRANDEDNESS: single
            (D) TOPOLOGY: linear (ii) MOLECULE TYPE: DNA (vi) ORIGINAL SOURCE:

(xi) SEQUENCE DESCRIPTION: SEQ ID NO: 6:

TTTTTCTAGA TCTGGA                                                     16

(2) INFORMATION FOR SEQ ID NO: 7:

(i) SEQUENCE CHARACTERISTICS:

(A) LENGTH: 16
            (B) TYPE: nucleic acid
            (C) STRANDEDNESS: single
            (D) TOPOLOGY: linear (ii) MOLECULE TYPE: DNA (vi) ORIGINAL SOURCE:

(xi) SEQUENCE DESCRIPTION: SEQ ID NO: 7:

TTTTTCTAGA TCTGGA                                                      16

(2) INFORMATION FOR SEQ ID NO: 8:

(i) SEQUENCE CHARACTERISTICS:
            (A) LENGTH: 16
            (B) TYPE: nucleic acid
            (C) STRANDEDNESS: single
            (D) TOPOLOGY: linear (ii) MOLECULE TYPE: DNA (vi) ORIGINAL SOURCE:

(xi) SEQUENCE DESCRIPTION: SEQ ID NO: 8:

TTTTTCTAGA TCTGGA                                                      16

(2) INFORMATION FOR SEQ ID NO: 9:

(i) SEQUENCE CHARACTERISTICS:
            (A) LENGTH: 16
            (B) TYPE: nucleic acid
            (C) STRANDEDNESS: single
            (D) TOPOLOGY: linear (ii) MOLECULE TYPE: DNA (vi) ORIGINAL SOURCE:

(xi) SEQUENCE DESCRIPTION: SEQ ID NO: 9:

TCCAGATCTA GAAAAA                                                      16

(2) INFORMATION FOR SEQ ID NO: 10:

(i) SEQUENCE CHARACTERISTICS:
            (A) LENGTH: 10
            (B) TYPE: nucleic acid
            (C) STRANDEDNESS: single
            (D) TOPOLOGY: linear (ii) MOLECULE TYPE: DNA (vi) ORIGINAL SOURCE:

(xi) SEQUENCE DESCRIPTION: SEQ ID NO: 10:

GCGTTTTGCT                                                             10

(2) INFORMATION FOR SEQ ID NO: 11:

(i) SEQUENCE CHARACTERISTICS:
            (A) LENGTH: 10
            (B) TYPE: nucleic acid
            (C) STRANDEDNESS: single
            (D) TOPOLOGY: linear (ii) MOLECULE TYPE: DNA (vi) ORIGINAL SOURCE:

(xi) SEQUENCE DESCRIPTION: SEQ ID NO: 11:

GCGTTTTGCT                                                                 10

CHIMERAS OF SULFUR-LINKED OLIGONUCLEOTIDE ANALOGS AND DNA AND RNA

This application is a continuation-in-part of U.S. application Ser. No. 08/068,981, filed May 28, 1993, now abandoned, which is a divisional application of U.S. application Ser. No. 07/202,528, filed Jun. 6, 1988, now U.S. Pat. No. 5,216,141.

BACKGROUND OF THE INVENTION

1. Field of the Invention

This invention relates to nucleic acids, more specifically to nucleic acid analogs, more specifically to nucleic acid analogs that have linking group and base substitutions that make the more stable to degradation, broaden their recognition powers, and improve their ability to form tertiary structures. This spefication makes reference to the patent application entitled "Oligonucleotide Analogs Containing Sulfur", Ser. No. 07/202,528 filed: Jun. 6, 1988, issued on Jun. 1, 1993 as U.S. Pat. No. 5,216,141, and Ser. No. 08/068,981, a continuation-in-part of Ser. No. 07/202,528 that is co-pending with this application, and related to Ser. No. 07/594,290, issued as U.S. Pat. No. 5,432,272 on Jul. 11, 1995, and Ser. No. 08/375,132, a continuation-in-part of Ser. No. 07/594,290 that is co-pending with this application. Ser. No. 07/202,528 discloses compositions of matter that are DNA and RNA analogs where the bridging phosphodiester linkages are replaced by dimethylene sulfone groups. The claims that have been allowed in Ser. No. 07/594,290 and that are pending in Ser. No. 08/068,981 refer to compositions where all of the phosphodiester linking groups have been so replaced. The claims in this continuation cover compositions of matter where only some of the linking phosphates are replaced. Since the instant compositions contain both phosphate and dimethylenesulfone linkages, they are referred to as oligonucleotide-sulfone chimeras, or more simply, chimeras. Ser. No. 08/375,132 claims compositions of matter that are oligonucleotide analogs and contain non-standard nucleobases. The compositions claimed in this application includes non-standard nucleobases.

2. Description of the Related Art Background

Deoxyribonucleic acid (DNA) and ribonucleic acid (RNA) are molecules central to biological processes. As oligomers composed of five subunits (adenosine, A, cytidine, C, guanosine, G, uridine, U, and thymidine, T) joined by phosphodiester linkages, naturally occurring nucleic acids possess two notable structural properties.

First, oligonucleotides bind to complementary oligonucleotides (where "complementarity rules" are defined such that A in one oligonucleotide strand is paired against either U or T in the other, and G in one oligonucleotide strand is paired against C in the other, with the two strands anti-parallel) to form helical structures. The binding specificity is due to hydrogen bonds formed between bases on one oligonucleotide strand and complementary bases on the other. The thermodynamically stability of the helical structures is in part due to hydrophobic forces between bases stacked on top of each other in the double helical structure.

Second, information is coded in the oligonucleotide by the order of bases in the oligonucleotide strand. This information codes for proteins and nucleic acids necessary for the growth and replication of organisms. Oligonucleotides with define sequence serve as genes, genetic regulatory agents, intracellular messages, especially for the synthesis of proteins, and possibly intercellular messages.

Natural oligonucleotides have widespread value in the laboratory, in diagnostic systems, and as therapeutic agents. However, natural oligonucleotides are degraded in biological environments due to the action of enzymes, particularly deoxyribonucleases (DNases), ribonucleases (RNases), and phosphodiesterases (Plesner, P.; Goodchild, J.; Kalckar, H. M.; Zamecnik, P. C. Proc. Nat. Acad. Sci. 1987 84 1936–1939). This limits their value in many applications.

Many workers have successfully stabilized oligonucleotides to enzymatic degradation by replacing the phosphate linking groups with another. Analogs of oligonucleotides where the phosphate bridging group is replaced by a carboxyl group has also been synthesized (Jones, A. S.; MacCoss, M.; Walker, R. T. Biochem. Biophys. Acta 1973 365 365–377). The analogs slowly hydrolyzed upon standing at neutral pH, and the polymer with adenosine formed an undefined complex with polyuridylic acid. Analogously, carbamate analogs of oligonucleotides have been synthesized (Mungall, W. S.; Kaiser, J. K. J. Org. Chem. 1977 42 703–706). Oligonucleotides have been constructed that contain 1,3 propanediol units between normal phosphate bases (Seela, F.; Kaiser, K. Nucl. Acids Res. 1987 15 3113–3129). These last molecules are not isosteric analogs of DNA, and cannot be prepared in the modified structural forms needed to modulate their binding affinity for natural oligonucleotides (vide infra).

Recently, Miller, T'so, and their coworkers reported the synthesis of compounds that are isosteric analogs of DNA, differing only in that one oxygen of the phosphate group of each subunit is replaced by a methyl group. In all other structural aspects, these molecules are identical to naturally occurring oligonucleotides. These molecules, termed methylphosphonate DNA analogs, or methylphosphonates, lack phosphate-borne negative charges. A patent was recently awarded to the inventors of these molecules (U.S. Pat. No. 4,469,863, Sep. 4, 1984).

However, the methylphosphonates and many similar analogs themselves have several undesirable chemical properties. First, substitution of a methyl group for an oxygen at phosphorus creates a chiral center. Therefore, oligomers composed of methylphosphonate building blocks are again complex mixtures of diastereomers. Further, apparently only one diastereomer of a methylphosphonate-linked dinucleotide can bind to a complementary natural oligonucleotide (Miller, P. S.; Yano, J.; Yano, E.; Carroll, C.; Jayaraman, K.; Ts'o, P.O.P. Biochem. 1979, 18 5134–5143).

A second problem arises from the chemical instability of methylphosphonate diesters and similar analogs. As with triesters of phosphoric acid, diesters of methylphosphonates are readily hydrolyzed in base. Basic conditions are required for the deprotection of bases in the reported procedure for the synthesis of oligomethylphosphonates. Complete deprotection of the bases is critical for full biological activity, as protecting groups block the functional groups that form the hydrogen bonds to complementary oligonucleotides. In the synthesis of natural oligonucleotides, complete deprotection is normally achieved by prolonged exposure of the protected oligonucleotide with base. Phosphodiester groups present in natural oligonucleotides are stable under these conditions. Methylphosphonate diesters are not.

SUMMARY OF THE INVENTION

Related applications (Ser. No. 07/202,528, issued, as U.S. Pat. No. 5,216,141, and Ser. No. 08/068,981, copending with this application) discloses oligonucleotide analogs where all linking phosphates in an oligonucleotide are replaced by dimethylene sulfide, sulfoxide, and sulfone units. The claims made in this application differs from previous applications in that they cover compositions of matter that are oligonucleotide analogs, but where only some of the units in the oligomer chain are joined by dimethylenesulfide, sulfoxide, and sulfone units, while others remain phosphodiester linkages or other linker modifications known in the art.

These linkages have advantages over those already known in the art in that they are (in the sulfide and sulfone forms) free of diastereomerism, and are fully stable under both enzymatic and alkaline conditions. Chimeric oligonucleotide analogs have an advantage over the analogs where all phosphodiester linkages are replace by dimethylenesulfone linkers in that they retain some of the negative charges of natural DNA, and therefore retain much of the water-solubility of natural oligonucleotides. Further, fully substituted oligosulfones have a rich conformational versatility through intramolecular interactions that are not obstructed by coulombic repulsion between backbone anionic groups. Fully natural DNA, due to the polyanionic nature of the backbone, exist frequently in an extended structure. Chimera have an intermediate behavior, forming structure in solution more than natural oligonucleotides, but less than fully substituted oligosulfones.

BRIEF DESCRIPTION OF THE DRAWING

The FIGURE depicts a schematic diagram showing the synthetic route to a sulfone-linked building unit described in Examples 1 to 3.

DETAILED DESCRIPTION OF THE INVENTION AND PREFERRED EMBODIMENTS

This invention relates to oligonucleotide analogs where some of the linking phosphate diester groups are replaced by dimethylenesulfone units. In the preferred embodiment, the analog contains at least 1 dimethylenesulfide, dimethylenesulfoxide, or dimethylenesulfone unit, but with fewer than 50% of the units replaced. The linkages containing sulfur can link consecutive nucleoside analogs in the chain, or can be interspersed with phosphate linkages or other linkages known in the art. In the preferred embodiment, the nucleobases carried by the oligonucleotide chimera are selected from the group consisting of adenine, thymine, uracil, guanine, and cytosine. However, non-standard nucleobases such as those disclosed in Ser. Nos. 07/594,290 and 08/375,132 are useful in diagnostics, and some embodiments will incorporate non-standard nucleobases and functionalized nucleobases (e.g, those where the 5-position of a pyrimidine carries a side chain) as replacements for standard bases.

In its preferred embodiment, the compositions of the invention are synthesized from building blocks that have nucleoside analogs joined by a thioether, sulfoxide, or sulfone, each being a precursor for the following compound in this list, where functionality on the nucleobase has been protected as in the synthesis of standard oligonucleotide synthesis, where the 5'-end of the sulfone unit it protected as a dimethoxytrityl group, and the 3'-end activates as a phosphoramidite unit. In this way, chimeras can be prepared by solid phase synthesis as conveniently as are natural oligonucleotides.

In the preferred embodiment, the chimeras are from 2 to 200 units in length, more preferably from 5 to 100 units, most preferably from 10 to 50 units in length.

For the segment of the chimera that is linked by sulfone units, procedures disclosed in Ser. No. 07/202,528, Ser. No. 08/068,981, Ser. No. 07/594,290, and Ser. No. 07/594,290 are used. The building blocks for the synthesis of the oligonucleotide analogs consist of four parts: (a) a linking moiety bearing (b) a single sulfhydryl group (—SH) (c) a single unprotected hydroxyl group (—OH, most preferably a primary alcohol group), and (d) a suitably protected base analog. An oligonucleotide analog with the desired sequence of building blocks is synthesized by stepwise condensation of the appropriate building blocks onto a growing oligonucleotide analog chain. The sequence involves reaction of the free hydroxyl group of a growing oligomer chain with methanesulfonyl chloride, reaction of the resulting methanesulfonate with the thiolate anion of the next building block, and finally oxidation (if desired) of the resulting thioether to the sulfoxide or sulfone.

Depending on whether the desired product is (a) the sulfide, (b) the sulfoxide, or (c) the sulfone, the thioether is (a) not oxidized, (b) oxidized with 1 equivalent of aqueous hydrogen peroxide at 0° C., or (c) oxidized with potassium hydrogen persulfate ($KHSO_5$).

To join the sulfur-linked segment with the phosphate linked segment, adapter nucleoside analogs are required. When the adapter is joined to a sulfur-linked part of the chimera in the 5'direction and the phosphate-linked part of the chimera in the 3'-direction, the adapter nucleoside analog must have a 5'-carbon extension (that is, it must be a 5'-homonucleoside). When the adapter is joined to a sulfur-linked part of the chimera in the 3'-direction and the phosphate-linked part of the chimera in the 5'-direction, the adapter nucleoside analog must have a 3'carbon extension (that is, it must be a 3'-homonucleoside).

Detailed procedures for preparing these are provided in the Examples.

For the segment of the chimera that is linked by phosphate units, standard oligonucleotide synthetic procedures, well known to those of ordinary skill in the art, are used.

EXAMPLES

Example 1

Synthesis of 3'-Homothymidine

Literature on the Synthesis of 3'-homothymidine

Sanghvi Y. S., Bharadwaj R., Debart F., De Mesmaeker A.(1994) Efficient and stereoselective synthesis of 3'-Deoxy 3'-C-branched-Chain substituted thymidine. *Synthesis* 1163–1166.

Sanghvi Y. S., Ross B., Bharadwaj R., Vasseur J.-J. (1994) An easy access of 2',3'Dideoxy-3'-α-C-formyl-adenosine and -guanosine analogs via stereoselective C—C bond forming radical reaction. *Tet. Lett.* 35, 4697–4700.

1-(3S,4R)-(5-O-(tert-Butyldiphenylsilyl)-2-deoxy-β-pentofuranosyl)thymine

Thymidine (450 mg; 1.86 mmol) and DMAP (4-dimethylaminopyridine, 2 mg; 16.4 μmol) were dried over a period of 1 h under high vacuum at 50° C., and dissolved under argon in anhydrous pyridine (2.5 mL). Over a period of 1 h, TBDPSCl (TBDPS=tert-butyldiphenylsilyl, 360 μL; 1.41 mmol) was added at room temperature (RT) and the mixture was stirred for 3 h. Additional TBSPSCl (160 μL; 0.63 mmol) was added over a period of 30 min, and the mixture was stirred overnight at RT. By TLC, the thymidine was completely converted to 5'TBDPSO-thymidine, with traces of doubly protected thymidine visible by TLC.

The reaction mixture was then concentrated by evaporation under reduced pressure and the residue taken up in MeOH (2 mL). The solution was added dropwise into a vigorously stirred mixture of ether/petroleum ether/$H_2O$ (1:4:11.5; 17 mL), from which the product precipitated as a white solid. The suspension was stirred for 115 min, and then allowed to stand 1 h at RT. The product was recovered by filtration and repeatedly washed with $H_2O$. The product was dried for 24 h in a desiccator over $P_2O_5$ under vacuum to yield 1-(3S,4R)-(5-O-(tert-butyldiphenylsilyl)-2-deoxy-β-pentofuranosyl)thymine (791 mg, 1.65 mmol 87%) of a white solid, which contained traces of 3',5'-diTBDPSO-thymidine as an impurity.

$R_f$-value: 5'-TBDPSO-thymidine: 0.27 ($CH_2Cl_2$:MeOH=97:3); 3',5'-diTBDPSO-thymidine: 0.67

FAB-MS (NOBA matrix): m/z (%)=481 (M+H$^+$, 22); 423 (15); 406 (21); 405 (63); 385 (23); 337 (16); 335 (11); 325 (10), 319 (16); 287 (12); 279 (13); 217 (11), 270 (30), 269 (100), 267 (10), 259 (21); 257 (11); 251 (15); 247 (12); 240 (13); 239 (45); 227 (22); 223 (10), 213 (18), 207 (19); 200 (17); 199 (73); 198 (26); 197 (97) (reporting only ions with m/z>195).

UV ($CH_2Cl_2$) $\lambda_{max}$[nm]($\epsilon$ in M$^{-1}$cm$^{-1}$)=266 (9300); 229 (7500).

IR ($CHCl_3$) ν (cm$^{-1}$)=3390, 3180, 3070, 3050, 3010, 2960, 2930, 2860, 1690, 1470, 1430, 1385, 1370, 1320, 1310, 1290, 1270, 1240, 1190, 1115, 1065, 1020, 1005, 960, 935, 910, 880, 855, 820, 805, 705.

$^1$H-NMR ( $CDCl_3$; 200 MHz): δ (ppm)=1.09 (s, 9H, $CH_3$(t-Bu)); 1.63 (d, J=1.1, 3H, $CH_3$(T)); 2.19 (ddd, J=13.5, 8.2, 6.0, 1H, H-2'); 2.42 (ddd, J=13.5, 5.7, 2.4, 1H, H-2'); 270 (br, 1H, OH); 3.82–3.89 (m, 2H, H-5'); 4.00 (m, 1H, H4'); 4.56 (m, 1H, H-3'), 641 (dd, J=8.2, 5.7, 1H, H-1'); 7.35–7.46 (m, 5H, H arom.); 7.48 (d, J=1.1, 1H, H-6); 7.64–7.67 (m, 6H, H arom.); 9.07 (br, 1H, NH).

$^{13}$C-NMR ($CDCl_3$; 50 MHz): δ (ppm)=11.84 (q, $CH_3$(T)); 19.10 (s, t-Bu); 26.73 (q, t-Bu); 40.73 (t, $C_2$'); 63.87 (t, $C_5$'); 71.97 (d, $C_3$); 84.43 (d, $C_4$'); 86.78 (d, $C_1$'); 110.98 (s, $C_5$); 127.69 (d, CH arom.); 127.74 (d, CH arom.); 129.80 (d, CH arom.); 129.90 (d, CH arom.); 132.07 (s, C arom.); 132.58 (s, C arom.); 135.02 (d, CH arom.); 135.26 (d, $C_6$); 150.18 (s, $C_2$); 163.50 (s, $C_3$).

β-Tributyltinstyrene

Phenylacetylene (1.67 mL; 15.2 mmol) was heated at reflux in benzene (17 mL) in a dry two necked flask with a reflux condenser under argon. The heating bath was removed and AIBN (13 mg; 79 μmol) added. $Bu_3SnH$ (5 mL; 18.9 mmol) was added dropwise over a period of 30 min under gentle reflux, and the mixture was then heated for 1.5 h under reflux. The benzene was removed by distillation at atmospheric pressure under argon, and the product recovered by distillation under high vacuum (ca. 0.1 Torr; 160° C.) to yield β-tributyltinstyrene (5.21 g, 13.3 mmol, 87%) as a colorless liquid. The trans:cis was 85:15 according to $^1$H-NMR.

1-(3S,4R)-(5-O-(tert-Butyldiphenylsilyl)-3-O-(tolyloxythiocarbonyl)-2-deoxy-βpentofuranosyl)thymine 1-(3S,4R)-(5-O-(tert-Butyldiphenylsilyl)-2-deoxy-β-pentofuranosyl)thymine(5.89 g; 12.3 mmol) and N-hydroxysuccinimide (563 mg; 4.89 mmol) were dried overnight under high vacuum, and dissolved under argon in pyridine (3.5 mL) and benzene (40 mL). After incubating for 30 min under argon, tolylchlorothionoformate (3.1 mL; 20 mmol) in benzene (10 mL) was added dropwise over a period of 1 h at 50° C. The temperature was raised to 70° C. and the now clear mixture was stirred for a period of 3 h . The mixture was cooled to RT and the solution removed by suction from the precipitate under argon. The residue was washed twice with benzene (4 mL). The combined benzene solutions containing product were directly used in the next step. For an analytical sample, a portion of the material was chromatographed over silica gel ($CH_2Cl_2$:MeOH=97:3).

$R_f$-value: 0.22 ($CH_2Cl_2$:MeOH=98:2)

FAB-MS (NOBA matrix): m/z (%)=631 (M+H$^+$, 6); 573 (12); 505 (13); 464 (16); 463 (41); 405 (24); 270 (10); 269 (38); 259 (11), 239 (20); 227 (12); 207 (13); 199 (30), 198 (12), 197 (50) (reporting only ions with m/z>195).

UV ($CH_2Cl_2$) $\lambda_{max}$ [nm] ($\epsilon$ in M$^-$cm$^{-1}$)=265 (11800); 229 (13000).

IR ($CHCl_3$) ν (cm$^{-1}$)=3075, 3010, 2950, 2930, 2860, 1705, 1690, 1505, 1470, 1430, 1315, 1290, 1270, 1190, 1115, 1005, 970, 955, 925, 820, 820, 705.

$^1$H-NMR ( $CDCl_3$; 300 MHz): δ (ppm)=1.12 (s, 9H, t-Bu); 1.65 (s, 3H, $CH_3$(T)); 2.39 (s, 3H, $CH_3$(toluene)); 2.26 (m, 1H, H-2'); 2.75 (m, 1H, H-2'); 4.08 (br, 2H, H-5'); 4.38 (br, 1H, H-4'); 5.95 (d, J=6.0, H-3'); 6.53 (dd, J=9.3, 5.3, 1H, H-3'); 6.98–7.73 (m, 14H arom., H-6).

$^{13}$C-NMR ($CDCl_3$; 75 MHz): δ (ppm)=12.10 (q, $CH_3$(T)); 19.41 (s, $CH_3$ (t-Bu)); 21.01 (q, $CH_3$ (toluene)); 27.03 (q, $C(CH_3)_3$); 38.16 (t, $C_2$'); 64.74 (t, $C_5$'); 83.98; 84.54; 84.84 (3d, $C_1$'; $C_3$', $C_4$'); 111.63 (s, $C_5$); 121.40; 127.90; 128.10; 130.20; 130.29; 131.80; 132.69; 134.87; 135.26; 135.65; 136.64 (d, $C_6$); 150.35 (s, $C_2$); 151.22 (s, C arom.); 163.67 ($C_4$); 194.56 (s, C=S).

1-(3S,4R)-(3-C-Styryl-5-O-(tert-butyldiphenylsilyl)-2,3-dideoxy-β-pentofranosyl)thymine The crude solution of 1-(3S,4R)-(5-O-(tert-Butyldiphenylsilyl)-3-O-(tolyloxythiocarbonyl)-2-deoxy-β-pentofuranosyl)thymine (ca. 10.6 mmol) in benzene (60 mL) was transferred under argon to a two necked flask. β-Tributyltinstyrene (11 g; 27.5 mmol) was added. After 30 min at 40° C. under argon, the mixture was heated for 72 h under reflux. The reactions temperature reduced slowly to 40° C. and AIBN added in a stream of argon, to prevent entrance of air, in 10 portions (10×300 mg; 18.3 mmol). The mixture was cooled to RT and directly loaded onto a silica gel column (200 g silica gel; petroleum ether; petroleum ether:ethyl acetate=95:5 to 1:1) to yield 1-(3S,4R)-(3-C-styryl-5-O-(tert-butyldiphenylsilyl)-2,3-dideoxy-βpentofuranosyl)thymine (2.75 g, 4.86 mmol, 39.5%) as a white solid.

$R_f$-value: 0.35; 2,3 Dideoxyderivative: 0.29 (ethyl acetate:petroleum ether=1:1)

FAB-MS (NOBA matrix): m/z (%)=567 (M+H$^+$, 11); 509 (13); 442 (16), 441 (34); 398 (11); 397 (27); 384 (11), 283 (25); 363 (12); 337 (26); 269 (23); 247 (14); 245 (15); 241 (12); 239 (15); 233 (11); 227 (13), 225 (11); 223 (11), 200 (15); 199 (47); 198 (18); 197 (51) (Only ions with m/z>195 are reported).

UV (CH$_2$Cl$_2$) $\lambda_{max}$[nm] ($\epsilon$ in M$^-$cm$^{-1}$)=260 (15700); 229 (8700).

IR (CHCl$_3$) ν (cm$^{-1}$)=3030, 3010, 2960, 2930, 2860, 1700, 1685, 1470, 1430, 1265, 1010, 1005, 965,905, 820, 705.

$^1$H-NMR (CDCl$_3$, 200 MHz): δ (ppm)=1.12 (s, 9H, t-Bu); 1.63 (s, 3H, CH$_3$(T)); 2.33–2.47 (m, 2H, H-2'); 3.32 (m, 1H, H-3'); 3.80–3.91 (m, 2H, H-5'); 4.11 (m, 1H, H-4'); 6.00 (ddd, J=15.8, 8.3, 1H, CH=CH); 6.20 (dd, J=6.7, 3.3, 1H, H-1'); 6.50 (d, J=15.8, 1H, CH=CH); 7.28–7.48 (m, 6H, H arom.); 7.57 (d, J=1.1, 1H, H-6); 7.64–7.71 (m, 4H, H arom.); 8.44 (br, 1H, NH).

$^{13}$C-NMR (CDCl$_3$, 50 MHz): δ (ppm)=11.90 (q, CH$_3$(T)); 19.22 (s, C(CH$_3$)$_3$); 26.80 (q, C(CH$_3$)$_3$); 39.51 (t, C$_{2'}$); 40.91 (d, C$_{3'}$); 62.28 (t, C$_{5'}$); 84.50 (d, C$_{4'}$); 85.53 (d, C$_{1'}$) 110.37 (s, C$_5$); 125.95; 126.94; 127.53; 127.63; 128.35; 129.70; 132.44; 132.75; 132.89; 135.08; 135.23; 136.18 (d, C$_6$); 150.06 (s, C$_2$); 150.06 (s, C$_4$); 163.60 (s, C$_4$).

1-(3S,4R)-(3-C-Formyl-5-O-(tert-butyldiphenylsilyl)-2,3-dideoxy-β-pentofiranosyl)thymine 1-(3S,4R)-(3-C-Styryl-5-O-(tert-butyldiphenylsilyl)-2,3-dideoxy-β-pentofuranosyl)thymine (926 mg; 1.64 mmol) and 4-methylmorpholine N-oxide (211 mg; 1.78 mmol) were dissolved in dioxane (9 mL) and OsO$_4$ was added (9 mL; 54 μmol; 2.5% in t-BuOH) in the dark. The mixture was stirred 1.5 h at RT and NaIO$_4$ (608 mg; 2.84 mmol) and H$_2$O (1 mL) was added. The mixture was stirred a further 3 h at RT and the resulting suspension filtered through celite. The residue was repeatedly washed with ethyl acetate. The filtrate was treated with H$_2$O and extracted three times with ethyl acetate. The combined organic phases were dried over MgSO$_4$ and concentrated. The crude product was chromatographed (20 g silica gel CH$_2$Cl$_2$:MeOH=98:2 to 96:4) to yield 1-(3S,4R)-(3-C-formyl-5-O-(tert-butyldiphenylsilyl)-2,3-dideoxy-β-pentofuranosyl)thymine (480 mg, 976 μmol; 59%) as a white solid.

$R_f$-value: 0.4 (CH$_2$Cl$_2$:MeOH=97:3)

1-(3S,4R)-(3-C-Hydroxymethyl-5-O-(tert-butyldiphenylsilyl)-2,3-dideoxy-βpentofiranosyl)thymine 1-(3S,4R)-(3-C-Formyl-5-O-(tert-butyldiphenylsilyl)-2,3-dideoxy-βpentofuranosyl)thymine (375 mg; 0.76 μmol) was dissolved in EtOH (3 mL) and NaBH$_4$ (9 mg; 0.92 μmol) was added. The reaction mixture was stirred for 1.5 h at RT, and the excess NaBH$_4$ destroyed with 3M HOAc. The solution was extracted three times with ethyl acetate against saturated NaCl solution, and the combined organic phases dried over MgSO$_4$. The solution was concentrated and the product dried under high vacuum to yield 1-(3S,4R)-(3-C-hydroxymethyl-5-O-(tert-butyldiphenylsilyl)-2,3-dideoxy-β-pentofuranosyl)thymine (375 mg; 0.76 μmol, 100%).

$R_f$-value: 0.24 (CH$_2$Cl$_2$:ethyl acetate=1:1)

FAB-MS (NOBA matrix): m/z (%)=517 (M+Na$^+$, 12); 496 (12); 495 (M+H$^+$, 29733); 437 (21); 312 (11); 311 (37); 293 (11); 292 (14); 291 (45); 289 (16); 272 (10); 269 (16); 247 (19); 241 (14); 239 (21); 237 (14); 233 (18); 227 (13), 225 (16); 223 (14); 221 (23); 215 (11); 213 (20); 211 (12); 207 (16); 201 (18); 200 (25); 199 (100); 198 (27); 197 (94) (Only ions with m/z>195 are reported).

UV (CH$_2$Cl$_2$) $\lambda_{max}$[nm] ($\epsilon$ in M$^{-1}$cm$^{-1}$)=267 (9600); 228 (6600)

$^1$H-NMR (CDCl$_3$; 500 MHz): δ (ppm)=1.10 (s, 9H, t-Bu), 1.64 (d, J=1.2, 3H, CH$_3$(T)); 2.12 (m, 1H, H-2'); 2.33 (quintet, J=6.7, 1H, H-2'); 2.60 (m, 1H, H-3'); 3.64 (dd, J=10.9, 6.2, 1H, H-3"); 3.67 (dd, J=10.9, 5.8, 1H, H-3"); 3.82 (dd, J=11.2, 3.2, H-5'); 3.95 (m, 1H, H-4'); 4.01 (dd, J=11.2, 3.5, 1H, H-5'); 6.13 (t, J=6, 1H, H-1'); 7.37–7.47 (m, 7H, H-6, H arom.); 7.66–7.68 (m, 4H, H arom.), 9.19 (br, 1H, NH).

$^{13}$C-NMR (CDCl$_3$; 125 MHz): δ (ppm)=12.18 (q, CH$_3$(T)); 19.37 (s, C(CH$_3$)$_3$); 26.99 (q, C(CH$_3$)$_3$); 35.57 (t, C$_{2'}$); 41.62 (d, C$_{3'}$); 63.32; 64.98 (2t, C$_3$", C$_{5'}$); 83.18 (d, C$_{4'}$); 84.30 (d, C$_{1'}$); 110.90 (s, C$_5$); 127.92, 127.96; 130.03; 130.11 (4d, CH arom.); 132.57; 133.03 (2s, C arom.); 135.41; 135.58 (2d, C$_6$, CH arom.); 150.50 (s, C$_2$); 163.97 (s, C$_4$).

1-(3S,4R)-(3-C-(S-Acetylthiomethyl)-5-O-(tert-butyldiphenylsilyl)-2,3-dideoxy-βpentofuranosyl)thymine PPh$_3$ (370 mg; 1.44 mmol) and 1-(3S,4R)-(3-C-hydroxymethyl-5-O-(tert-butyldiphenylsilyl)-2,3-dideoxy-β-pentofuranosyl)thymine (355 mg; 718 μmol) were separately dried for 30 min at 40° C. under high vacuum, and then separately dissolved under argon in THF (THF= tetrahydrofuran, each 6 mL). To the PPh$_3$ solution was added DIAD (275 μL; 1.44 mmol) at 0° C., the mixture stirred 15 min at 0° C. stirred to yield a light yellow suspension. To this suspension were added at 0° C. 1-(3S,4R)-(3-C-hydroxymethyl-5-O-(tert-butyldiphenylsilyl)-2,3-dideoxy-β-pentofuranosyl)thymne dissolved in THF (6 mL) and then AcSH (103 μL; 1.44 mmol). The reaction mixture was under stirring slowly warmed to RT and then concentrated. The crude product was chromatographed (30 g silica gel; ethyl acetate:CH$_2$Cl$_2$=1:4 bis 1:1) to yield 1-(3S,4R)-(3-C-(S-acetylthiomethyl)-5-O-(tert-butyldiphenylsilyl)-2,3-dideoxy-β-pentofaranosyl)thymine (238 mg, 444 μmol; 62%) as a white foam.

$R_f$-value: 0.67 (ethyl acetate:CH$_2$Cl$_2$=1:1)

FAB-MS (NOBA matrix): m/z (%)=554 (17); 553 (M+H$^+$, 48); 496 (12), 495 (37); 428 (17); 427 (49); 385 (26); 370 (14); 369 (46); 367 (17); 351 (13); 349 (14); 328 (12); 327 (41), 293 (12); 257 (11); 249 (18); 247 (20); 289 (13), 284 (10); 283 (37); 241 (34); 239 (31); 237 (13), 229

(15); 227 (11); 225 (14); 223 (15); 222 (15); 221 (66), 215 (15), 213 (11); 207 (12); 205 (11); 200 (22); 199 (96); 198 (25); 197 (100) (Only ions with m/z>195 are reported).

$^1$H-NMR (CDCl$_3$; 300 MHz): δ (ppm)=1.10 (s, 9H, CH$_3$ (t-Bu)); 1.61 (d, J=1.1, 3H, CH$_3$(T)); 2.22 (m, 2H, H-2'); 2.34 (s, 3H, CH$_3$(Ac)); 2.69 (m, 1H, H-3'); 2.95 (m, 2H, H-3"); 3.82 (m, 2H, H-5'); 4.07 (m, 1H, H4'); 6.14 (t, J=5.9, 1H, H-1'); 7.37–7.47 (m, 10H, 9H arom., H-6); 7.66–7.70 (m, 6H, H arom.); 8.68 (br, 1H, NH).

$^{13}$C-NMR (CDCl$_3$; 50 MHz): δ (ppm)=11.89 (q, CH$_3$(T); 19.15 (s, C(CH$_3$)$_3$); 21.69 (t, C$_{3''}$); 26.75 (q, C(CH$_3$)$_3$); 30.30 (q, CH$_3$(Ac)); 37.55; 37.95 (t, d, C$_2$, C$_3$); 63.57 (t, C$_{5'}$); 84.22; 84.56 (2d, C$_{1'}$, C$_4$); 110.52 (s, C$_5$); 127.68; 129.71; 129.80; 132.31; 132.77; 134.99 (d, C$_6$); 135.08; 135.27; 150.03 (s, C$_2$); 163.54 (s, C$_3$); 194.50 (s, C=O).

1-(3S,4R)-(3-C-Mercaptomethyl-5-O-(tert-butyldiphenylsilyl)-2,3-dideoxy-βpentofuranosyl)thymine 1-(3S,4R)-(3-C-(S-Acetylthiomethyl)-5-O-(tert-butyldiphenylsilyl)-2,3-dideoxy-βpentofuranosyl)thymine (108 mg; 201 μmol) was dissolved in THF (1.5 mL) and MeOH (1.5 mL). The solution was frozen with N$_2$(l), evacuate under high vacuum, and warmed under argon to RT. This procedure was twice repeated. NaOH (2N; 0.4 mL; 402 μmol) was added at 0° C., where the NaOH solution was degassed in the same way. The reaction mixture was stirred for 1 h, and then treated with HOAc (3 M; 1 mL). The mixture was extracted three times with ethyl acetate and the combined organic phases dried over MgSO$_4$. The filtrate was concentrated and dried under high vacuum to yield 1-(3S, 4R)-(3-C-mercaptomethyl-5-O-(tert-butyldiphenylsilyl)-2, 3-dideoxy-β-pentofaranosyl)thymine (90 mg, 176 μmol; 88%) as a white foam.

R$_f$-value: 0.55 (CH$_2$Cl$_2$:MeOH=95:5)

FAB-MS (NOBA matrix): m/z (%)=511 (10); 453 (8); 327 (23); 308 (11); 307 (42); 273 (15); 249 (10); 247 (14); 229 (14); 221 (18); 200 (11); 199 (50); 198 (12); 197 (47); 187 (10), 183 (18); 181 (13); 179 (11); 167 (11); 165 (19); 163 (16); 161 (28); 155 (21); 154 (40); 153 (12); 152 (10); 139 (28); 138 (24); 137 (54); 136 (53); 135 (100); 129 (35); 128 (12); 127 (73); 123 (15); 121 (23); 120 (12); 119 (13); 117 (15); 115 (11); 111 (21); 107 (21); 105 (22) (Only ions with m/z>195 are reported).

$^1$H-NMR (CDCl$_3$; 400 MHz): δ (ppm)=1.11 (s, 9H, t-Bu); SH; 1.66 (d, J=1.2, 3H, CH$_3$(T)); 2.26 (m, 2H, H-2'); 2.51–2.61 (m, 3H, H-3", H-3'); 3.79 (dd, J=11.5, 3.3, 1H, H-5'); 3.87 (quintet, J=3.0, 1H, H-4'); 4.06 (dd, J=11.5, 2.7, 1H, H-5'); 6.13 (dd, J=6.6, 5.5, 1H, H-1'); 7.39–7.48 (m, 7H, H-6, H arom.); 7.52–7.69 (m, 4H, H arom.); 8.45 (br, 1H, NH).

$^{13}$C-NMR (CDCl$_3$; 75 MHz): δ (ppm)=12.25 (q, CH$_3$(T)); 19.42 (s, C(CH$_3$)$_3$); 26.66 (t, C$_{3''}$); 27.06 (q, C(CH$_3$)$_3$); 38.11 (t, C$_{2'}$); 41.37 (t, C$_2$); 64.24 (t, C$_{5'}$); 84.47 (d, C$_4$); 84.59 (d, C$_{1'}$); 110.86 (s, C$_5$); 127.95 (d, CH arom.); 128.00 (d, CH arom.); 130.07 (d, CH arom.); 130.17 (d, CH arom.); 132.61 (s, C arom.); 133.01 (s, C arom.); 135.41 (d, CH arom.); 135.59 (d, C$_6$); 150.41 (s, C$_2$); 164.04 (s, C$_3$).

Example 2

Synthesis of 5'-iodomethylthymidine

3'-t-Butyldiphenylsilyl-5'-deoxy-5'-iodothymidine

The reaction was carried out under argon with the exclusion of water. Thymidine (300 mg, 1.24 mmol) and triphenylphosphine (487 mg, 1.61 mmol) were placed in a reaction flask and dried under high vacuum (40° C., 1 h). The residue was dissolved under argon in anhydrous pyridine (3.5 mL). Iodine (407 mg, 1.6 mmol) in pyridine (2 mL) was added at 0° C., and the solution became violet. The cooling bath was removed and the reaction mixture was stirred for 3 h at RT. The solution remained light yellow (TLC: CH$_2$Cl$_2$/MeOH (9:1), R$_f$-value: 0.2 (thymidine), 0.54 (product)). The reaction mixture was taken up in CH$_2$Cl$_2$ (25 mL) and carefully washed with saturated NH$_4$Cl solution (25 mL). The organic phase was separated and the aqueous phase was re-extracted three times with CH$_2$Cl$_2$. The combined organic phases were dried over MgSO$_4$, filtered and the solvent was removed using a rotary evaporator. The crude product was dried under high vacuum and used directly for introduction of the 5'-TBDPS group.

The crude product of the preceding iodination (>1.2 mmol) and imidazole (168 mg, 2.4 mmol) were dried under high vacuum (1 h, 40° C.). The mixture was dissolved under argon in CH$_2$Cl$_2$ (3.5 mL). TBDPSCl (0.48 mL, 1.84 mmol) was added dropwise at 0° C. The cooling bath was then removed and the mixture stirred at RT for 2 h (TLC: CH$_2$Cl$_2$/MeOH (95:5), R$_f$-values: 0.22 (starting material), 0.6 (product)). Anhydrous MeOH (0.5 mL) was added and the mixture stirred a further 30 min. The reaction mixture was diluted with CH$_2$Cl$_2$ (25 mL) and washed with saturated NH$_4$Cl solution (25 mL). The aqueous phase was re-extracted three times with CH$_2$Cl$_2$. The combined organic phases were dried over MgSO$_4$, filtered and the solvent was removed using a rotary evaporator. The crude product was dried briefly under high vacuum and chromatographed on silica gel (30 g) with CH$_2$Cl$_2$/ethyl acetate (4:1). Fractions containing product were combined, the solvent was removed using a rotary evaporator and the residue was dried under high vacuum to yield 3'-t-Butyldiphenylsilyl-5'-deoxy-5'-iodothymidine as a colorless solid (575 mg, 0.93 mmol); yield over two steps: 78%.

TLC: CH$_2$Cl$_2$/MeOH (9:1), R$_f$-value: 0.54.

$^1$H-NMR (CDCl$_3$, 300 MHz): δ (ppm)=1.10 (s, 9H, t-Bu); 1.89 (s, 3H, CH$_3$-T); 1.98 (m, 1H, H-2'); 2.36 (dq, 1H, J=2.4, 13.5 Hz, H-2'); 2.79 (dd, 1H, J=4.2, 10.5 Hz, H-5'); 3.13 (dd, 1H, J=4.2, 10.5 Hz, H-5'); 3.71 (dd, 1H, J=3.6, 7.8 Hz, H4'); 4.21 (m, 1H, H-3'); 6.40 (dd, 1H, J=6,7.8 Hz, H-1'); 7.40–7.50 (m, 6H, p-,m-Ph); 7.48 (m, 1H, H-6); 7.63–7.70 (m, 4H, o-Ph); 8.92 (s, 1H, NH).

$^{13}$C-NMR (CDCl$_3$, 75 MHz): δ (ppm)=7.5 (C-5'); 12.6 (CH$_3$-T); 19.0 (C(CH$_3$)$_3$); 26.9 (C(CH$_3$)$_3$); 40.5 (C-2'); 76.2 (C-3'); 84.2, 84.4 (C-4', C-1'); 111.3 (C-5); 128.0, 128.1 (m-Ph); 130.2, 130.3 (p-Ph); 132.8, 132.9 (quaternary C-Ph); 135.7, 135.8 (C-6; o-Ph); 150.2 (C-2); 163.6 (C-4).

FAB-MS (NOBA matrix): m/z=591 (M$^+$, 25%); 533 (M$^+$-t-Bu, 3%);463 (M$^+$-I, 5%); 381 (5%); 361 (24%); 337.3 (M$^+$-I-thymine, 6%); 197.1 (37%); 135 (78%); (127 (I$^+$, 100%); Only ions with m/z>195 are reported.

IR (CHCl$_3$) ν (cm$^{-1}$)=3395 (NH); 2960, 2930, 2890, 2860 (CH); 1690 (CO, shoulder at 1710); 1470, 1430, 1360, 1275, 1115, 1105, 1050.

UV (CH$_2$Cl$_2$) λ$_{max}$ [nM] (ε in M$^{-1}$cm$^{-1}$)=265 (16',090).

1-(3'-t-Butyldiphenylsilyl-6'-isopropyloxysufonyl-2',5',6'deoxy-β-D-allo-furanosyl)-thymine The isopropyl ester of methanesulfonic acid (1.42 g, 10.2 mmol) was dissolved in anhydrous THF (6.5 mL) and anhydrous HMPT (2.5 mL). A solution of butyllithium (6.8 mL, 1.6 M in hexane) was added dropwise at −73° C. for 15 min and the mixture stirred for 1.5 h at −73° C. 3't-Butyldiphenylsilyl-5'-deoxy-5'-iodothymidine (1.008 g, 1.7 mmol) was dissolved in anhydrous THF (1.7 mL) and added dropwise for 15 min at −73° C. The reaction mixture was stirred for 2.5 h at −73° C. (TLC: petroleum ether/THF (9:4), R$_f$-values: 0.3 (starting material), 0.2 (product)).

The reaction was quenched by addition of NH$_4$Cl solution (1 M, 5 mL). The reaction mixture was diluted with diethyl ether and the organic phase washed with NH$_4$Cl solution (1 M). The aqueous phase was re-extracted with diethyl ether. The combined organic phases were dried over MgSO$_4$, filtered, concentrated and briefly dried under high vacuum. The crude product was chromatographed on silica gel (50 g) with petroleum ether/THF (9:4). Fractions containing product were combined, the solvent evaporated and the dried residue under high vacuum to yield 1-(3'-t-butyldiphenylsilyl-6'-isopropyloxysofonyl-2',5',6'-deoxy-βD-alo-furanosyl)-thymine as a colorless foam (790 mg, 1.3 mmol). Yield: 77%.

TLC: petroleum ether/THF (9:4), R$_f$-value: 0.2.

$^1$H-NMR (CDCl$_3$, 200 MHz): δ (ppm)=1.09 (s, 9H, t-Bu); 1.38 (d, 6H, J=6.2 Hz, CH$_3$-iPr); 1.88 (s, 3H, CH$_3$-T); 1.75–1.98 (m, 3H, H-2', H-5'); 2.32 (dq, 1H, H-2'); 2.75–3.12 (m, 2H, H-6'); 3.87 (m, 1H, H-4'); 4.09 (m, 1H, H-3'); 4.90 (sept, 1H, J=6.2, CH-iPr); 6.33 (dd, 1H, J=6.2, 7.6 Hz, H-1'); 6.89 (d, 1H, J=1.3, H-6); 7.35–7.52 (m, 6H, p-,m-Ph); 7.60–7.69 (m, 4H. o-Ph); 9.02 (s, 1H, NH).

$^{13}$C-NMR (CDCl$_3$, 50 MHz): δ (ppm)=12.2 (CH$_3$-T); 18.7 (C(CH$_3$)$_3$); 22.8 (CH$_3$-iPr); 26.6 (C(CH$_3$)$_3$); 27.3 (C-5'); 39.1 (C-2'); 47.5 (C-6'); 75.4, 76.2 (C-3', CH-iPr); 83.8, 84.6 (C-4', C-1'); 111.4 (C-5); 127.7, 127.8 (m-Ph); 129.9, 130.1 (p-Ph); 132.5 (quaternary C-Ph); 134.6 (C-6); 135.4 (o-Ph); 150.2 (C-2); 163.6 (C-4).

FAB-MS (NOBA matrix): m/z=601.1 (M+H$^+$, 1%); 355 (6.4%); 327 (10%); 281.1 (10%); 207.1 (21%); 147.1 (45%); 136 (40%); 127 (25%); 91 (40%); 72.9 (100%); (Only ions with m/z>70 are reported).

IR (CHCl$_3$) ν (cm$^{-1}$)=3395 (NH); 2960, 2930, 2860 (CH); 1690 (CO, shoulder at 1710); 1470, 1430, 1360, 1335, 1260, 1170, 1115, 1105, 1050,930, 890.

UV (CH$_2$Cl$_2$) λ$_{max}$ [nm] (ε in M$^-$cm$^{-1}$)=266 (13',400).

1-(3'-t-Butyldiphenylsilyl-6'-iodo-2',5',6'-deoxy-β-D-allo-furanosyl)-thymine 1-(3'-t-Butyldiphenylsilyl-6'-isopropyloxysufonyl-2',5',6'-deoxy-β-D-alo-faranosyl)thyine (1.35 g, 2.25 mmol) and triphenylphosphine (3.56 g, 13.5 mmol) were placed in a round bottom flask, coevaporated with toluene, dried under high vacuum, and dissolved in anhydrous benzene (9 mL). The colorless solution was stirred at RT, and iodine (2.29 g, 9.02 mmol) was added as solid to yield a yellow-brown suspension. The mixture was heated in a 90° C. bath to reflux for 2 h. (TLC: petroleum ether/THF (9:4), R$_f$-values: 0.07 (PPh$_3$O), 0.18 (starting material), 0.25 (side product), 0.29 (product), 0.55 (PPh$_3$S), 0.8 (PPh$_3$)). The reaction was stopped when traces of a polar side product were observed by TLC. The reaction was cooled to RT, diluted with ethyl acetate, and then washed with saturated sodium thiosulfate and saturated NaCl solutions. The aqueous phases were re-extracted with ethyl acetate three times. The combined organic phases were dried over MgSO$_4$, filtered, concentrated and briefly dried under high vacuum. The crude product was chromatographed on silica gel (260 g, 2 cm column) with petroleum ether/THF (9:3, 250 mL; 9:4, 500 mL). Fractions containing product were combined, the solvent was removed by rotary evaporation, and the residue was dried under high vacuum to yield 1-(3'-t-butyldiphenylsilyl-6'-iodo-2',5',6'-deoxy-β-D-allo-faranosyl)-thymine as a colorless solid (457 mg, 0.756 mmol, 33%). Mixed fractions (70 mg; product:starting material=6:4) yielded recovered starting materials (513 mg, 0.854 mmol).

TLC: petroleum ether/THF (9:4), R$_f$-value: 0.3.

$^1$H-NMR (CDCl$_3$, 300 MHz): δ (ppm)=1.09 (s, 9H, t-Bu); 1.75 (m, 2H, H-5'); 1.85–1.90 (m, 1H, H-2'); 1.88 (s, 3H, CH$_3$-T); 2.35 (dq, 1H, H-2'); 2.95–3.00, 3.04–3.08 (2×m, 2H, H-6'); 3.93 (m, 1H, H-4'); 4.07 (m, 1H, H-3'); 6.27 (dd, 1H, J=6.2, 7.3 Hz, H-1'); 6.89 (d, 1H, J=1.3, H-6); 7.39–7.49 (m, 6H, p-,m-Ph); 7.62–7.67 (m, 4H, o-Ph); 8.72 (s, 1H, NH).

$^{13}$C-NMR (CDCl$_3$, 75 MHz): δ (ppm)=0.5 (C-6'); 12.6 (CH$_3$-T); 19.0 (C(CH$_3$)$_3$); 26.8 (C(CH$_3$)$_3$); 37.3 (C-5'); 39.8 (C-2'); 75.3 (C-3'); 85.0, 86.1 (C-4', C-1'); 111.3 (C-5); 127.9, 128.0 (m-Ph); 130.1, 130.2 (p-Ph); 132.95, 132.96 (quaternary C-Ph); 135.1 (C-6); 135.7, 135.8 (o-Ph); 150.1 (C-2); 163.4 (C-4).

FAB-MS (NOBA matrix): m/z=605 (M$^+$, 4%); 391.2 (58%); 375 (9%); 289 (10%); 285 (7%); 279 (8%); 222 (7%); 199 (6%); 197 (7%); 179 (5%); 167 (27%); 1.65 (10%); 154 (80%); 149 (91%); (Only ions with m/z>140 are reported).

IR (CHCl$_3$) ν (cm$^{-1}$)=3395 (NH); 2960, 2930, 2900, 2860 (CH); 1690 (CO, shoulder at 1710); 1470, 1430, 1365, 1270, 1115, 1105, 1085; 1050; 1010; 1005; 830, 705.

UV (CH$_2$Cl$_2$) λ$_{max}$ [nm] (ε in M$^{-1}$cm$^{-1}$)=265 (11',900).

Analysis: C$_{27}$H$_{33}$N$_2$O$_4$SiI Calc. C, 53.64; H, 5.50; N, 4.63. Found: C, 53.55; H, 5.29; N. 4.50

Example 3

The Dimer Building Unit RO-Tso$_2$T-OR

TBDPSO-Tso$_2$T-OTBDPS

Cs$_2$O$_3$ (156 mg; 160 μmol) was dried for 1 h under high vacuum at 50° C. The iodide 1-(3't-butyldiphenylsilyl-6'-iodo-2',5',6'-deoxy-β-D-allo-furanosyl)-thymine (97 mg; 480 μmol) was added and the mixture was dried for 30 min under high vacuum at 30° C. The thiol 1-(3S,4R)-(3-C-mercaptomethyl-5-(-(tert-butyldiphenylsilyl)-2,3-dideoxy-β-pentofuranosyl)thymne (90 mg; 176 μmol) was separately dried overnight under high vacuum at RT, dissolved under argon in anhydrous THF (3 mL), and added to the mixture of iodide and $Cs_2CO_3$. The suspension was degassed several times under vigorous stirring under house vacuum with argon, and stirring continued under argon at RT. After 3 h, no further progress in the reaction was observable, and DMF (dimethylformamide, 1 mL) was added. The mixture was again degassed for 30 min using the house vacuum and stirring continued under argon at RT. After a total of 7 h, acetate buffer (2 mL; 3 M HOAc; 1 M NaOAc) was added, the mixture diluted with $H_2O$ and extracted three timed with $CH_2Cl_2$. The combined organic phases were dried over $MgSO_4$, concentrated and dried under high vacuum.

The crude thioether-dimer (170 mmol) was dissolved in THF (3.8 mL) and MeOH (25 mL), and a solution of Oxone (420 mg) and NaOAc (188 mg) in $H_2O$ (6.3 mL) was added over a period of 5 min. The white suspension was stirred at RT for 1.5 h, and then concentrated to a third of its volume. The suspension was diluted with $CH_2Cl_2$ and extracted with saturated $Na_2S_2O_3$ solution. The aqueous phase was re-extracted twice with $CH_2Cl_2$ and the combined organic phases dried over $MgSO_4$. The crude product was chromatographed (20 g silica gel; $CH_2Cl_2$:ethyl acetate:$H_2O$=80:20:0.25 with 3–8% MeOH) to yield TBDPSO-$Tso_2$T-OTBDPS as a white solid (148 mg; 145 μmol; 91%).

$R_f$-value: TBDPSO-$Tso_2$T-OTBDPS: 0.20; thiol: 0.45; iodide: 0.53 ($CH_2Cl_2$:MeOH=95:5)

FAB-MS (NOBA matrix): m/z (%)=1021 (14); 1020 (28); 1019 (M+H$^+$, 47); 963 (11); 962 (20); 961 (36); 941 (15); 893 (11); 837 (11); 836 (18); 835 (33); 816 (19); 815 (36); 769 (10); 768 (20); 767 (40), 711 (10); 710 (17); 709 (33); 690 (17); 689 (34); 579 (17) 559 (18); 512 (15); 511 (40); 554 (15); 453 (43); 434 (14); 433 (44); 351 (27); 307 (32); 293 (11); 287 (12); 273 (15); 267 (11); 255 (13); 247 (35); 239 (16); 225 (15); 207 (11); 200 (11); 199 (43);198 (17); 197 (58)(Only ions with m/z>195 are reported).

UV ($CH_2Cl_2$) $\lambda_{max}$ [nm] (ε in M$^{-1}$cm$^{-1}$)=266 (17000); 228 (12600)

$^1$H-NMR (CDCl$_3$; 300 MHz): δ (ppm)=1.08 (s, 9H, t-Bu); 1.09 (s, 9H, t-Bu); 1.67 (d, J=1.1, 3H, CH$_3$(T)); 1.78 (m, 2H, H-5(T$_2$)); 1.88 (d, J=1.0, 3H, CH$_3$(T$_2$)); 2.14–2.36 8M, 3H, 2H-2'(T$_2$), H-2'(T$_1$)); 2.43–2.52 (m, 1H, H-2'(T$_1$)?); 2.70–2.78 (m, 1H, H-3'(T$_1$)?); 2.80–2.98 (m, 2H, H-6'(T2)); 3.02–3.13 8m, 2H, H-3"((T$_1$)); 3.83 (dd, J=11.2, 3.0, 1H, H-5'(T$_1$)); 3.84–3.90 (m, 2H, H-4'); 4.00 (dd, J=11.2, 2.7, 1H, H-5'(T$_1$)); 4.17 (m, 1H, H-3'(T$_2$)); 6.11–6.18 (m, 2H, H-1'); 6.90 (d, J=1.2, 1H, H-6(T$_2$)); 7.33–7.48 (m, 13H, 12H arom., H-6 (T$_1$)); 7.50–7.68 (m, 8H, H arom.); 8.75 (br, 1H, NH); 8.90 (br, 1H, NH):

$^{13}$C-NMR (CDCl$_3$; 75 NMz): δ (ppm)=12.25 (q, CH$_3$(T)); 12.44 (q, CH$_3$(T)); 19.06 (s, C(CH$_3$)$_3$); 19.36 (s, C(CH$_3$)$_3$); 25.42 (t, C$_{5'}$(T$_2$)); 26.89 (q, C(CH$_3$)$_3$); 32.39 (d, C$_3$'(T1)?); 38.24 (t, C$_{2'}$); 38.54 (t, C$_{2'}$?); 50.65 (t, C$_6$(T$_2$)); 55.00 (t, C$_{3''}$(T$_1$)); 63.81 (t, C$_5$(T$_1$)); 75.91 (d, C$_3$(T$_2$)); 84.23 (d, C$_{4'}$); 84.59 (d, C$_{4'}$); 87.30 (d, C$_{1'}$); 11.51 (s, C$_5$); 127.96, 128.02 (2d, CH arom.); 130.07; 130.14; 130.28; 130.34 (4d, CH arom.); 132.24; 132.80; 132.80; 132.93 (4s, C arom.); 135.37; 135.59; 135.69; 135.74 (4d, CH arom.); 136.50 (d, C$_6$); 150.16 (s, C$_2$); 150.45 (s, C$_5$); 163.62 (s, C$_4$).

HO-$Tso_2$T-OH

Dimer TBDPSO-$Tso_2$T-OTBDPS (116 mg; 114 mmol) was dried under high vacuum, dissolved in a glass flask under argon in anhydrous pyridine (0.5 mL), and transferred to a plastic test tube with a rubber septum. The flask was washed with pyridine (0.2 mL) and the washings transferred to the plastic test tube. A HF solution (0.7 mL; 4.7 M) was added and the mixture stirred for 16 h at RT. Excess HF was destroyed with methoxytrimethylsilane (4 mL) with stirring for 30 min. The solution was transferred to a round bottom flask, and the plastic test tube washed with a $CH_2Cl_2$/MeOH mixture. The combined organic phases were concentrated and the crude product dried under high vacuum. The product was then chromatographed (22 g silica gel; $CH_2Cl_2$:EtOH:MeOH=86:7:7, 0.25% $H_2O$, 100 mL; $CH_2Cl_2$:EtOH:MeOH=83:9:8, 0.25% $H_2O$, 200 mL) to yield HO-$Tso_2$T-OH as a white glass (52 mg; 96 μmol; 84%).

$R_f$-value: 0.05 ($CH_2Cl_2$:ethyl acetate:MeOH=4:6:1)

FAB-MS (NOBA matrix): m/z=545 (13); 544 (29); 543 (M+, 100); 542 (13) (Only ions with m/z>500 are reported).

UV ($CH_2Cl_2$:MeOH=1:1) $\lambda_{max}$ [nm] (ε in M$^{-}$cm$^{-1}$)=267 (15000); 225 (5800)

$^1$H-NMR (DMSO:D$_2$O=4:1; 300 MHz): δ (ppm)=1.74 (d, J=1.1, 3H, CH$_3$(T)); 1.76 (d, J=1.1, 3H, CH$_3$(T)); 1.93 (m, 1H, H-5'(2)); 2.02–2.11 (m, 2H, H-2'(2), H-5'(2)), 2.18–2.30 (m, 3H, 2H-2'(1), H-2'(2)); 2.69 (m, 1H, H-3'(1)); 3.13–3.25 (m, 3H, 2H-6'(2), H-3"(1)); 3.36 (dd, J=13.8, 3.6, 1H, H-3"(1)); 3.58 (dd, J=12.7, 3.4, 1H, H-5'(1)); 3.69–3.76 (m, 3H, H-5'(1), 2H-4'); 4.12 (m, 1H, H-3'(2)); 5.96 (dd, J=6.3, 4.0, 1H, H-1'(1)); 6.09 (t, J=7, 1H, H-1'(2)); 7.36 (d, J=1.1, 1H, H-6); 7.80 (d, J=1.1, 1H, H-6).

$^{13}$C-NMR (DMSO; 75 MHz): δ (ppm)=11.96 (q, CH$_3$(T)); 12.19 (q, CH$_3$(T)); 24.87 (t, C$_5$D(T$_2$)); 31.01 (d, C$_{3'}$(T$_1$)); 37.61 (t, C$_{2'}$); 37.99 (t, C$_{2'}$); 49.35 (C$_{6'}$(T$_2$)); 53.43 (t, C$_{3''}$(T$_1$)); 60.05 (t, C$_5$(T$_1$)); 72.45 (d, C$_3$(T$_2$)); 83.32; 83.68; 84.00; 84.62 (4d, C, C$_{4'}$); 109.73 (s, C$_5$); 109.89 (s, C$_5$); 136.09 (d, C$_6$); 150.22 (s, C$_2$); 150.35 (s, C$_2$); 163.58 (s, C$_4$); 163.71 (s, C$_4$).

DMTrO-$Tso_2$T-OH

The completely deprotected dimer HO-$Tso_2$T-OH(85 mg; 157 μmol) was coevaporated with pyridine and dried overnight under high vacuum. DMAP (a few grains) was added, and the mixture dissolved under argon in anhydrous pyridine (2 mL) and TEA (55 μΛ; 0.39 mmol). DMTrCl (DMT=dimethoxytrityl, 110 mg; 314 μmol) was added and the mixture stirred for 2 h at RT. The reaction was quenched with MeOH and the mixture concentrated. Residual pyridine was removed by coevaporation once with toluene, and the crude product chromatographed (5 g silica gel; $CH_2Cl_2$:MeOH=98:2, 95:5, 90:10 with 2% TEA) to yield DMTrO-$Tso_2$T-OH as a white foam (132 mg, 156 μmol; 99%), which contained some TEA as impurity.

$R_f$-value: 0.33 ($CH_2Cl_2$:MeOH=95:5)

UV ($CH_2Cl_2$) $\lambda_{max}$ [nm] (ε in M$^{-1}$cm$^{-1}$)=266 (19500); 238 (21800)

FAB-MS (NOBA matrix): m/z=867 (M+Na$^+$, 5); 844 (14), 319 (M+H$^+$, 11); 305 (13); 304 (52); 303 (100), 289 (14). (Only ions with m/z>100 are reported).

¹H-NMR (DMSO; 400 MHz): δ (ppm)=1.50 (d, J=1.1, 3H, CH₃(T)); 1.77 (d, J=1.1, 3H, CH₃(T)); 1.96 (m, 1H, H-5'(T₂)); 2.03–2.14 (m, 2H, H-5'(T₂), H-2'(T₂)); 2.26 (m, 1H, H-2'(T₂)); 2.32–2.40 (m, 2H, H-2'(T₁)); 2.92 (td, J=8.9, 3.7, 1H, H-3'(T₂)); 3.12–3.35 (m, 6H, CH₂SO₂CH₂, H-5' (T¹)); 3.70 (m, 1H, H-4'(T₁)); 3.73 (2s, 3H, OCH₃); 3.89 (m, 1H, H-4'(T₂)); 4.13 (m, 1H, H-3'(T₂)); 5.34 (br, 1H, OH); 6.06 (dd, J=7.0, 4.8, 1H, H-1'(T₁)); 6.14 (t, J=7.0, 1H, H-1'(T₂)); 6.87 (m, 4H, H arom.); 7.20–7.31 (m, 7H, H arom.); 7.38–7.42 (m, 3H, 2H arom., H-6);7.53 (d, J=1.1, 1H, H-6).

¹³C-NMR (DMSO; 100 MHz): δ (ppm)=11.85; 11.99 (2q, CH₃(T)); 25.01 (t, C₅·(T₂)); 31.91 (d, C₃·(T₁)); 37.21; 38.09 (2t, C₂·); 49.47 (t, C₆·(T₂)); 53.61 (t, C₃·(T₁)); 54.97 (q, OCH₃); 62.95 (t, C₅·(T₁)); 72.82 (d, C₃·(T₂)); 82.59; 83.42; 83.70; 84.23 (4d, C₄·, C₁·); 85.82 (s, C(ar)₃); 109.24, 109.93. (2s, C₅); 113.18; 126.72; 127.62; 127.83; 129.70 (5d, CH arom); 135.28; 135.34 (2s, C arom.); 135.71; 136.11 (2d, C₆); 144.67 (s, C arom.); 150.26; 150.39 (2s, C₂); 158.10; 158.11 (s, COCH₃); 163.62; 163.70 (2s, C₄).

Preparation of the Tso₂T phosphoramidite

The 5'-tritylated TT dimer DMTrO-Tso₂T-OH(100 mg; 118 μmol) was dried together with DIPAT (10 mg; 58 μmol) for 1 h at 40° C. under high vacuum, placed under an atmosphere of argon, and dissolved in CH₃CN (0.5 mL). Bis-diisopropylamino-β-cyanoethoxyphosphin (51 μL; 157 μmol) was added and the mixture stirred 3 h at RT. The workup consisted of extraction with saturated NaHCO₃ solution and CH₂Cl₂. The aqueous phase was re-extracted twice with CH₂Cl₂ and the combined organic phases washed with saturated NaCl solution and dried over MgSO₄. The concentrated residue was dissolved in CH₂Cl₂ (2 mL) and the produced precipitated by adding hexane (20 mL) for 20 min. at −20° C. The product was recovered by centrifugation, the clear supernatant removed by pipette, concentrated and again treated with CH₂C₂/hexane. The combined residues were dried under high vacuum to yield DMTrO-Tso₂T-O-phosphoramidite (113 mg, 108 μmol; 92%) as a white foam.

Rf-value: 0.4 (petroleum ether:acetone:TEA=4.5:4.5:1)

FAB-MS (NOBA matrix): m/z=1046 (34); 1045 (M+H⁺, 62); 613 (13); 460 (19), 308 (13); 307 (31), 305 (10), 304 (37); 303 (100); 289 (20)(Only ions with m/z>200 are reported).

UV (CH₂Cl₂) $\lambda_{max}$ [nm] (ε in M⁻cm⁻¹)=266 (21500); 238 (23700)

¹H-NMR (CDCl₃; 300 MHz): δ (ppm)=1.18 (m, 12H, (CH₃)₂CH); 1.56 (s, 3H, CH₃(T)); 1.91; 1.92 (2s, 3H, CH₃(T)); 2.12 (m, 1H); 2.27–2.51 (m, 5H); 2.60 (m, 1H); 2.65 (m, 2H, CH₂CN); 3.01–3.20 (m, 4H, CH₂SO₂CH₂); 3.33 (dd, J=11, 3, 1H, H-5'(T₁)); 3.53 (m, 1H, H-5'(T₁)); 3.58–3.74 (m, 4H, CH₂OP, CH(CH₃)₂); 3.78 (s, 6H, CH₃O); 3.83–4.03 (m, 2H, H-4'); 4.37 (m, 1H, H-3'(T2)); 6.04 (t, J=6.8, 0.5H, H-1'); 6.09 (t, J=6.5, 0.5H, H-1'); 6.17 (t, J=4.3 0.5H, H-1'); 6.18 (t, J=4.7, 0.5H, H-1'); 6.83 (m, 4H, H arom.); 7.03 (d, J=1.0, 0.5H H-6); 7.04 (d, J=1.0, 0.5H, H-6); 7.22–7.32 (m, 7H, H arom.); 7.40–7.43 (m, 2H, H arom.); 7.53 (d, J=1.0, 0.5H, H-6); 7.54 (d, J=0.5H, H-6).

³¹P-NMR (CDCl₃, 120 MHz) δ (ppm)=148.75 (s); 149.38 (s).

Example 4

Synthesis of 3'-homoadenosine Derivatives

Literature on the Synthesis of 3'-homoadenosine Derivatives

Sanghvi Y. S., Bharadwaj R., Debart F., De Mesmaeker A.(1994) Efficient and stereoselective synthesis of 3'-Deoxy 3'-C-branched-Chain substituted thymidine. *Synthesis* 1163–1166.

Sanghvi Y. S., Ross B., Bharadwaj R., Vasseur J.-J. (1994) An easy access of 2',3'-Dideoxy-3'-α-C-formyl-adenosine and -guanosine analogs via stereoselective C—C bond forming radical reaction. *Tet. Lett.* 35, 4697–4700.

9-(3S,4R)-(5-O-(tert-Butyldiphenylsilyl)-2-deoxy-β-pentofuranosyl)adenine

2'-Deoxyadenosine monohydrate (5 g; 18.6 mmol) was dissolved in DMF (40 mL) and coevaporated twice with pyridine (each 50 mL) under high vacuum, to remove the water of crystallization. The DMF solution was diluted under argon with DMF (20 mL) and imidazole (3 g; 44.6 mmol) was added. TBDPSCl (5.5 mL; 22.3 mmol) was added for 30 min at RT and the reaction mixture stirred overnight at RT. MEOH (3 mL) was added and the DMF removed under high vacuum at 40° C. The resulting oil was chromatographed (60 g silica gel; CH₂Cl₂:MeOH=98:2 bis 95:5). 9-(3S,4R)-(5-O-(tert-Butyldiphenylsilyl)-2-deoxy-β-pentofuranosyl)adenine was isolated as an impure oil (11.8 g; 130%) and was used without further purification directly in the next step. For an analytical sample, a small sample was chromatographed with a 50-fold amount of silica gel (CH₂Cl₂:MeOH=95:5).

R$_f$-value: 0.33 (CH₂Cl₂:MeOH=90:10)

FAB-MS (NOBA matrix): m/z (%)=492 (14); 191 (38); 490 (M+H⁺, 77); 432 (22); 199 (18); 197 (16); 163 (12); 162 (26); 154 (15); 137 (27); 136 (100); 135 (35) (only ions with m/z>100 are reported).

UV (CH₂Cl₂) $\lambda_{max}$ [nm] (ε in M⁻¹cm⁻¹)=260 (13300); 228 (7900).

IR (CHCl₃) ν (cm-1)=3510, 3410, 3070, 3050, 3000, 2960, 2930, 2860, 1630, 1590, 1470, 1430, 1360, 1330, 1295, 1245, 1110, 1105, 1000, 935, 910, 820, 700.

¹H-NMR (CDCl₃; 300 MHz): δ (ppm)=1.05 (s, 9H, t-Bu); 3.54 (ddd, J=13.3, 6.1, 3.7, 1H, H-2'); 2.72 (m, 1H, H-2'); 3.85 (dd, J=11.1, 3.8, 1H, H-5'); 3.93 (dd, J=11.1, 4.7, 1H, H-5'); 4.14 (m, 1H, H-4'); 4.75 (m, 1H, H-3'); 6.11 (br, 2H, NH₂); 6.49 (t, J=6.5, 1H, H-1'); 7.30–7.44 (m, 6H, H arom.); 7.60–7.67 (m, 4H, H arom.); 8.04 (s, 1H, H-8); 8.28 (s, 1H, H-2).

¹³C-NMR (CDCl₃; 75 MHz): δ (ppm)=19.24 (s, C(CH₃)₃); 26.94 (q, C(CH₃)₃); 40.74 (t, C₂·); 63.98 (t, C₅·); 71.84 (d, C₃·); 84.28 (d, C₄·); 87.15 (d, C₁·); 119.86 (s, C₅); 127.87 (d, CH arom.); 129.97 (d, CH arom.); 132.72 (s, C arom.); 132.82 (s, C arom.); 135.49 (d, CH arom.); 135.56 (d, CH arom.); 138.71 (d, C₈); 149.41 (s, C₄); 152.93 (d, C₂); 155.54 (s, C₆).

9-(3S,4R)-(5-O-(tert-Butyldiphenylsilyl)-3-O-(tolyloxythiocarbonyl)-2-deoxy-βpentofuranosyl)adenine 9-(3S,4R)-(5-O-(tert-Butyldiphenylsilyl)-2-deoxy-β-pentofuranosyl)adenine (11.8 g; 18.6 mmol) and DMAP(5.3 g; 43.4 mmol) were coevaporated with pyridine and dried under high vacuum at 40° C. The residue was dissolved under argon in anhydrous $CH_3CN$ (15 mL) and O-p-tolylchlorothionoformate (3.8 mL; 24.6 mmol) was added for 30 min. The reaction mixture was stirred overnight at RT. The resulting yellow suspension was concentrated, extracted three times with ethyl acetate against a 1N $HCl:H_2O$ (1:1); again with saturated $NaHCO_3$ solution, then with saturated NaCl solution and the combined organic phases were dried over $MgSO_4$. The brown oily crude product was chromatographed (100 g silica gel; $CH_2Cl_2$:MeOH=98:2 bis 94:6) to yield 9-(3S,4R)-(5-O-(tert-butyldiphenylsilyl)-3-O-(tolyloxythiocarbonyl)-2-deoxy-β pentofuranosyl)adenine as a yellow oil (8.05 g; 12.6 mmol; 68% over 2 steps).

$R_f$-value: 0.48 ($CH_2Cl_2$:MeOH=95:5)

FAB-MS (NOBA matrix): m/z (%)=642 (30); 641 (60); 640 (M+H$^+$, 100); 583 (17); 582 (36); 136 (17); 135 (10) (Only ions with m/z>100 are reported).

UV ($CH_2Cl_2$) $\lambda_{max}$ [nm] ($\epsilon$ in $M^{-1}cm^{-1}$)=258 (15500); 229 (13300)

IR ($CHCl_3$) ν (cm–1)=3410, 3070, 3050, 3000, 2960, 2930, 2860, 1630, 1585, 1505, 1470, 1430, 1365, 1290, 1275, 1230, 1190, 1115, 1070, 1005, 970, 940, 920, 820, 700.

$^1$H-NMR ($CDCl_3$, 400 MHz): δ (ppm)=1.09 (s, 9H, $CH_3$(t-Bu)); 2.38 (s, 3H, $CH_3$(Tol)); 2.88 (ddd, J=14.1, 5.5, 1.4, 1H, H-2'),; 2.99 (ddd, J=14.1, 8.9, 5.8, 1H, H-2'); 4.03 (d, J=3.4, 2H, H-5'); 4.47 (td, J=3.4, 1.5, 1H, H-4'); 5.88 (br, 2H, $NH_2$); 6.04 (m, 1H, H-3'); 6.57 (dd, J=8.9, 5.5, 1H, H-1'); 7.00 (m, 2H, H arom.); 7.22–7.46 (m, 8H, H arom); 7.64–7.69 (m, 4H, H arom.); 8.09 (s, 1H, H-8); 8.32 (s, 1H, H-2).

$^{13}$C-NMR ($CDCl_3$; 100 MHz): δ (ppm)=19.27 (s, C($CH_3$)$_3$); 20.98 (q, $CH_3$(Tol)); 26.97 (q, C($CH_3$)$_3$); 38.41 (t, $C_{2'}$); 64.31 (t, $C_{5'}$); 77.04; 79.13; 84.20 (3d, $C_{1'}$, $C_{3'}$, $C_{4'}$); 119.95 (s, $C_5$); 121.42, 127.92; 127.95; 130.03; 130.19 (5d, CH arom.); 132.40; 132.65 (2s, C arom.); 135.52; 135.64 (2d, CH arom.); 136.60 (s, C arom.); 138.41 (d, $C_8$); 149.81 (s, C arom.); 151.25 (s, $C_4$); 153.19 (d, $C_2$); 155.55 (s, $C_6$); 194.40 (s, C=S).

Analysis: Calc. C, 63.82; H, 5.83; N, 10.95; O, 10.00; Si, 4.39; S, 5.01. Found: C, 63.75; H, 5.74; N, 10.89; S, 4.83.

9-(3S,4R)-(3-C-Styryl-5-O-(tert-butyldiphenylsilyl)-2,3-dideoxy-β-pentofuranosyl)adenine 9-(3S,4R)-(5-O-(tert-Butyldiphenylsilyl)-3-O-(tolyloxythiocarbonyl)-2-deoxy-β-pentofuranosyl)adenine (3.69 g; 5.77 mmol) was dried over a weekend in a desiccator over $P_2O_5$ under high vacuum. β-Tributyltinstyrene was dissolved in benzene (20 mL) and transferred into a dry 50 mL two necked flask with a reflux condenser. β-Tributyltinstyrene (4.0 mL; 11.5 mmol) was added and for 30 min, the flask evacuated under house vacuum, and placed under an argon atmosphere. AIBN (0.74 g; 4.53 mmol) was added and the mixture heated under reflux. Every 4 h, additional portions of AIBN (6 portions of 0.74 g each; 6×4.53 mmol) were added, and the reaction mixture cooled to 40° C. The mixture was then refluxed further. After 60–75 h had all of the starting materials reacted. The reaction mixture was cooled and directly applied to a silica gel column (300 g; petroleum ether) which was eluted with petroleum ether until no zinc compound was recovered. The compound was then eluted with $CH_2Cl_2$ (0.5–3% MeOH) to yield 9-(3S,4R)-(3-C-styryl-5-O(tert-butyldiphenylsilyl)-2,3-dideoxy-β-pentofuranosyl)adenine as a colorless oil (1.16 g, 2.02 mmol; 35%).

$R_f$-value: 0.19 (petroleum ether:ethyl acetate=5:1)

FAB-MS (NOBA matrix): m/z (%)=578 (22); 577 (60); 576 (M+H$^+$, 100); 575 (19); 518 (20); 199 (13); 197 (16); 137 (19); 136 (69); 135 (29); 117 (16); 115 (10) (only ions with m/z>100 are reported).

UV ($CH_2Cl_2$) $\lambda_{max}$ [nm] ($\epsilon$ in $M^{-1}cm^{-1}$)=258 (17600); 229 (8300).

IR ($CHCl_3$) ν (cm–1)=3410, 3020, 2960, 2930, 2860, 1630, 1585, 1470, 1430, 1415, 1375, 1315, 1240, 1060, 820.

$^1$H-NMR ($CDCl_3$, 300 MHz): δ (ppm)=1.11 (s, 9H, $CH_3$(t-Bu)); 2.56 (ddd, J=13.5, 11.4, 6.9, 1H, H-2'); 2.70 (dd, J=13.5, 7.0, 1H, H-2'); 3.45 (m, 1H, H-3'); 3.80 (dd, J=11.6, 3.4, 1H, H-5'); 4.00 (m, 1H, H4'); 4.08 (dd, J=11.6, 2.5, 1H, H-5'); 5.81 (br, 2H, $NH_2$); 6.02 (dd, J=15.8, 8.2, 1H, CH=CH); 6.43 (dd, J=6.8, 1.5, 1H, H-1'); 6.50 (d, J=15.8, 1H, CH=CH); 7.26–7.43 (m, 11H, H arom.); 7.64–7.70 (m, 4H, H arom.); 8.34; 8.36 (2s, H-8, H-2).

$^{13}$C-NMR ($CDCl_3$; 50 MHz): δ (ppm)=18.96 (s, C($CH_3$)$_3$); 26.67 (q, C($CH_3$)$_3$); 39.83 (t, $C_{2'}$); 40.92 (d, $C_{3'}$); 62.65 (t, $C_{5'}$); 84.40 (d, $C_{4'}$); 86.06 (d, $C_{1'}$); 119.92 (s, $C_5$); 125.94; 126.46; 127.49; 128.31; 129.60; 129.79; 132.42; 132.52; 132.86; 135.23; 135.37; 136.23; 138.62 (d, $C_8$); 148.86 (s, $C_4$); 152.58 (d, $C_2$); 155.11 (s, $C_6$).

Analysis: Calc.: C, 70.92; H, 6.48; N, 12.16; O, 5.56; Si, 4.88. Found: C, 69.92; H, 6.49; N, 12.08.

9-(3S,4R)-(3-C-Formyl-5-O-(tert-butyldiphenylsilyl)-2,3-dideoxy-β-pentofuranosyl)adenine 9-(3S,4R)-(3-C-Styryl-5-O-(tert-butyldiphenylsilyl)-2,3-dideoxy-β-pentofuranosyl)adenine (620 mg, 1.08 mmol) and 4-methylmorpholine N-oxide were dissolved in dioxane (20 mL) and $H_2O$ (4 mL). $OsO_4$ (630 mL, 2.5% in t-BuOH; 62 μmol) was added in the dark and the mixture was stirred (3 h) at RT. $NaIO_4$ was added (1.07 g, 5 mmol). After 3 h, the suspension was passed through celite, which was washed with ethyl acetate. The filtrate was extracted with $H_2O$, and the aqueous phase re-extracted twice with ethyl acetate. The combined organic phases were dried over $MgSO_4$ and concentrated. The brown oily crude product was immediately chromatographed (20 g silica gel; $CH_2Cl_2$:MeOH= 98:2 to 92:8) to yield 9-(3S, 4R)-(3-C-formyl-5-O-(tert-butyldiphenylsilyl)-2,3-dideoxy-β-pentofuranosyl)adenine (390 mg, 778 mmol; 72%) as a slightly impure light brown oil.

$R_f$-value: product: 0.21; Diol: 0.18; 0.21($CH_2Cl_2$:MeOH= 95:5). FAB-MS (NOBA matrix): m/z (%)=504 (18); 503 (45); 502 (M+H$^+$, 100); 500 (23); 485 (20); 484 (47); 444 (23); 229 (11); 228 (39); 199 (18); 197 (25); 186 (14); 164 (12); 163 (11); 154 (13); 148 (17); 137 (24); 136 (71); 135 (48); 121 (11); 105 (13) (only ions with m/z>100 are reported).

$^1$H-NMR ($CDCl_3$, 300 MHz): δ (ppm)=1.06 (s, 9H, $CH_3$(t-Bu)); 2.86 (m, 2H, H-2'), 3.70 (m, 1H, H-3'); 3.06 (dd, J=11.0, 4.2, 1H, H-5'); 3.97 (dd, J=11.0, 5.3, 1H, H-5'); 3.42 (m, 1H, H4'); 5.86 (br, 2H, $NH_2$); 6.27 (dd, J=6.6, 4.6, 1H, H-1'); 7.32–7.47 (m, 6H, H arom.); 7.60–7.70 (m, 4H, H arom.); 8.01 (s, 1H, H-8); 8.29 (s, 1H, H-2); 9.78 (d, J=1.6, 1H, HCO).

$^{13}$C-NMR (CDCl$_3$; 75 MHz): δ (ppm)=19.22 (s, C(CH$_3$)$_3$); 26.88 (q, C(CH$_3$)$_3$); 32.83 (t, C$_{2'}$); 52.10 (d, C$_{3'}$); 64.59 (t, C$_{5'}$); 81.19 (d, C$_{4'}$); 85.19 (d, C$_{1'}$); 119.93 (s, C$_5$); 127.88; 130.01 (2d, CH arom.); 132.53; 132.86 (2s, C arom.); 135.50; 135.56 (2d, CH$_3$); 139.00 (d, C$_8$); 149.15 (s, C$_4$); 152.98 (d, C$_2$); 155.47 (s, C$_6$); 198.94 (s, C=O).

9-(3S,4R)-(3-C-Hydroxymethyl-5-O-(tert-butyldiphenylsilyl)-2,3-dideoxy-β pentofuranosyl)adenine 9-(3S,4R)-(3-C-Formyl-5-O-(tert-butyldiphenylsilyl)-2,3-dideoxy-β pentofuranosyl)adenine (158 mg, 315 μmol) was dissolved in a mixture of EtOH (1.5 mL) and THF (1.5 mL). NaBH$_4$ (6 mg; 157 μmol) was added, and the mixture stirred 2 h at RT. HOAc (3 M) was added until the reaction mixture no longer evolved gas. The reaction mixture was diluted with ethyl acetate and extracted with saturated NaCl solution. The aqueous phase was twice re-extracted with ethyl acetate and the combined organic phases dried over MgSO$_4$. The product was concentrated and dried under high vacuum to yield 9-(3S,4R)-(3-C-Hydroxymethyl-5-O-(tert-butyldiphenylsilyl)-2,3-dideoxy-β-pentofuranosyl)adenine (125 mg, 248 μmol, 79%) as a white foam.

R$_f$-value: 0.21 (CH$_2$Cl$_2$:MeOH=95:5)

FAB-MS (NOBA matrix): m/z (%)=506 (17); 505 (50); 504 (M+H$^+$, 100); 446 (25); 154 (11); 137 (13); 136 (33); 135 (13).

UV (CH$_2$Cl$_2$) λ$_{max}$ [nm] (ε in M$^{-1}$ cm$^{-1}$)=260 (18300); 235 (10600)

IR (CHCl$_3$) ν (cm−1)=3410, 3010, 2960, 2930, 2860, 1630, 1590, 1470, 1430, 1415, 1390, 1360, 1330, 1295, 1240, 1115, 1065, 820, 705.

$^1$H-NMR (CDCl$_3$, 300 MHz): δ (ppm)=1.07 (s, 9H, CH$_3$(t-Bu)); 2.44 (ddd, J=13, 9, 6.9, 1H, H-2'); 2.61 (ddd, J=13, 8, 3.4, 1H, H-2'); 2.78 (m, 1H, H-3'); 3.70 (d, J=5.88, 2H, H-3"); 3.83 (dd, J=11.0, 4.0, 1H, H-5'); 3.94 (dd, J=11.0, 4.7, 1H H-5'); 4.06 (m, 1H, H-4'); 6.13 (br, 2H, NH$_2$); 6.30 (dd, J=6.9, 3.4, 1H, H-1'); 7.32–7.45 (m, 6H, H arom.); 7.61–7.68 (m, 4H, H arom.); 8.11 (s, 1H, H-8); 8.30 (s, 1H, H-2).

$^{13}$C-NMR (CDCl$_3$; 75 MHz): δ (ppm)=19.20 (s, C(CH$_3$)$_3$); 26.90 (q, C(CH$_3$)$_3$); 36.20 (t, C$_{2'}$); 42.02 (d, C$_{3'}$), 62.91 (t, C$_{3''}$); 65.00 (t, C$_{5'}$); 84.28, 84.69 (2d, C$_{1'}$; C$_{4'}$); 119.94 (s, C$_5$); 127.87; 129.97; 130.02 (3d, CH arom.); 132.60; 132.70 (2s, C arom.); 135.53; 135.63 (2d, CH arom.); 138.62 (d, C$_8$); 149.15 (s, C$_4$); 152.86 (d, C$_2$); 155.52 (s, C$_6$).

9-(3S,4R)-(3-C-(S-Acetylthiomethyl)-5-O-(tert-butyldiphenylsilyl)-2,3-dideoxy-β pentofuranosyl)adenine PPh$_3$ (47 mg; 179 μmol) was dried for 1 h under high vacuum at 50° C. and dissolved under argon in THF (0.7 mL). DIAD (34 mL; 179 μmol) was added at 0° C. and the mixture stirred for 15 min to yield a white suspension. 9-(3S,4R)-(3-C-Hydroxymethyl-5-O-(tert-butyldiphenylsilyl)-2,3-dideoxy-β-pentofuranosyl)adenine (60 mg; 119 μmol) was dried at 30° C. under high vacuum and dissolved under argon in THF (0.7 mL). The solution was added at 0° C. added to a PPh$_3$-DIAD-suspension of AcSH (13 mL; 179 μmol). The now clear solution was stirred for 2 h and warmed slowly to RT. MeOH (1 mL) was added and the mixture concentrated. The oily residue was chromatographed (10 g silica gel; CH$_2$Cl$_2$:ethyl acetate=1:1 with 0–5% MeOH) to yield 9-(3S,4R)-(3-C-(S-acetylthiomethyl)-5-O-(tert-butyldiphenylsilyl)-2,3-dideoxy-β-pentofuranosyl)adenine (53 mg, 95 mmol, 79%) as a white foam.

R$_f$-value: 0.13 (CH$_2$Cl$_2$:ethyl acetate=1:1)

FAB-MS (NOBA matrix): m/z (%)=564 (10); 563 (23), 562 (M+H$^+$, 64); 307 (22); 289 (12); 197 (10), 191 (34); 178 (10), 155 (26), 154 (61), 152 (10); 139 (19); 138 (32); 137 (57); 136 (100); 135 (27); 124 (11); 123 (11); 121 (11); 120 (12); 115 (10); 107 (20); 105 (10)(only ions with m/z>100 are reported).

UV (CH$_2$Cl$_2$) λ$_{max}$ [nm] (ε in M$^{-1}$cm$^{-1}$)=259 (16600); 230 (13900)

IR (CHCl$_3$) ν (cm−1)=3410, 3020, 2960, 2930, 2860, 1690, 1630, 1585, 1470, 1430, 1415, 1360, 1330, 1295, 1245, 1135, 1110, 1050, 955, 820, 710.

$^1$H-NMR (CDCl$_3$, 300 MHz): δ (ppm)=1.08 (s, 9H, t-Bu); 2.33 (s, 3H, CH$_3$(Ac)); 2.35 (m, 1H, H-2'); 2.63 (ddd, J=13.5, 7, 3, 1H, H-2'); 2.81 (m, 1H, H-3'); 2.94 (dd, J=13.6, 7.2, 1H, H-3"); 3.03 (dd, J=13.6, 5.8, 1H, H-3"); 3.79 (dd, J=11.4, 3.5, 1H, H-5'); 3.89 (quintet, J=3.7, 1H, H-4'); 4.01 (dd, J=11.4, 3.4, 1H, H-5'); 6.05 (br, 2H, NH$_2$); 6.32 (dd, J=6.8, 3.0, 1H, H-1'); 7.34–7.46 (m, 6H, H arom.); 7.64–7.71 (m, 4H, H arom.); 8.17 (s, 1H, H-8); 8.31 (s, 1H, H-2).

$^{13}$C-NMR (CDCl$_3$; 50 MHz): δ (ppm)=18.93 (s, C(CH$_3$)$_3$); 26.65 (q, C(CH$_3$)$_3$); 29.65; 30.30 (q, t, CH$_3$(Ac), C$_{3''}$); 37.79; 38.19 (d, t, C$_{3'}$, C$_{2'}$); 63.57 (t, C$_{5'}$); 84.07 (d, C$_{4'}$); 85.16 (d, C$_{1'}$); 119.79 (s, C$_5$); 127.56; 129.59; 129.67 (3d, CH arom.); 132.43; 132.52 (2s, C arom.); 135.23; 135.37 (2d, CH arom.); 138.38 (d, C$_8$); 148.88 (s, C$_4$); 152.55 (d, C$_2$); 155.23 (s, C$_6$); 194.46 (s, C=S).

N$^6$-Benzoyl-9-(3S,4R)-(3-C-mercaptomethyl-5-O-(tert-butyldiphenylsilyl)-2,3-dideoxy-β pentofuranosyl)adenine 9-(3S,4R)-(3-C-(S-acetylthiomethyl)-5-O-(tert-butyldiphenylsilyl)-2,3-dideoxy-β pentofuranosyl)adenine (1.72 g; 3.07 mmol) and DMAP (345 mg; 3.07 mmol) were coevaporated with pyridine, dried under high vacuum and dissolved under argon in pyridine (15 mL). BzCl (Bz= benzyl, 1.72 mL; 15.3 mmol) was added and the mixture stirred at RT for 1 h. MeOH (1 mL) was added and the reaction mixture diluted with CH$_2$Cl$_2$. The mixture was extracted with saturated NaHCO$_3$ and the aqueous phase re-extracted twice with CH$_2$Cl$_2$. The combined organic phases were dried over MgSO$_4$, concentrated and dried under high vacuum.

The resulting brown oil was dissolved in pyridine (9 mL) and EtOH (18 mL). The mixture was degassed and placed under an argon atmosphere. A degassed solution of NaOH (2N, 9 mL) was added, and the mixture was stirred for 10 min. at RT, and then neutralized with HOAc (3M). Saturated NaHCO$_3$ solution was added and the aqueous solution extracted three times with CH$_2$Cl$_2$. The combined organic phases were dried over MgSO$_4$ and concentrated. The crude product was chromatographed (50 g silica gel; CH$_2$Cl$_2$:ethyl acetate=1:1 ) to yield N$^6$-benzoyl-9-(3S,4R)-(3-C-mercaptomethyl-5-O-(tert-butyldiphenylsilyl)-2,3-dideoxy- βpentofuranosyl)adenine (937 mg, 1.50 mmol, 49%) of a light yellow foam.

$R_f$-value: Intermediate: 0.86; thiol: 0.31($CH_2Cl_2$:ethyl acetate=1:1)

FAB-MS (NOBA matrix): m/z (%)=624 (M+H$^+$, 5); 241 (39); 240 (100); 199 (21); 197 (32); 183 (10)(only ions with m/z>160 are reported).

UV ($CH_2Cl_2$) $\lambda_{max}$ [nm] ($\epsilon$ in $M^{-1}cm^{-1}$)=260 (19400); 228 (19000).

IR ($CHCl_3$) ν (cm–1)=3410, 3070, 3010, 2960, 2930, 2860, 1710, 1670, 1615, 1585, 1505, 1470, 1455, 1430, 1390, 1330, 1295, 1240, 1110, 1090, 910, 710.

$^1$H-NMR ($CDCl_3$, 300 MHz): δ (ppm)=1.08 (S, 9H, T-Bu); 1.35 (T, J=8.2, 1H, SH); 2.41–2.67 (m, 3H, H-2', H-3'); 2.78 (m, 2H, H-3"); .3.81 (m, 1H, H-5'); 3.96–4.04 (m, 2H, H-4',H-5'); 6.39 (dd, J=6.9, 2.5, 1H, H-1'); 7.35–7.69 (m, 13H, H arom.); 8.34 (m, 2H, H arom.); 8.37 (s, H-8); 8.78 (s, H-2); 9.23 (br, 1H, NH).

$^{13}$C-NMR ($CDCl_3$; 75 MHz): δ (ppm)=19.22 (s, t-Bu); 25.99 (t, $C_{3''}$); 26.97 (q, t-Bu); 55.44 (t, $C_{2'}$); 41.39 (d, $C_{3'}$); 62.24 (t, $C_{5'}$); 84.89; 85.18 (2d, $C_{1'}$, $C_{4'}$); 123.51 (s, $C_5$); 127.90 128.06; 128.74; 129.99; 130.07; 132.69; 132.77 (7d, CH arom.); 133.76; 135.42 (2s, C arom.); 135.54; 135.64 (2d, CH arom.); 141.35 (d, $C_8$); 149.64 (s, $C_4$); 151.06 (s, $C_6$); 152.36 (d, $C_2$); 165.03 (s, C=O).

Example 5

Coupling of 3'-homoadenosine Derivatives with 5'-iodomethylthymidine Derivatives TBDPSO-A$^{Bz}$SO$_2$T-OTBDPS Iodide 1-(3'-t-butyldiphenylsilyl-6'-iodo-2',5',6'-deoxy-β-D-allo-furanosyl)-thymine (500 mg; 828 μmol) was dried together with $Cs_2CO_3$ (803 mg; 2.46 mmol) for 2 h at 40° C. under high vacuum, and then placed under an argon atmosphere. Thiol N$^6$-benzoyl-9-(3S,4R)-(3-C-mercaptomethyl-5-O-(tert-butyldiphenylsilyl)-2,3-dideoxy-β-pentofuranosyl)adenine (576 mg; 924 μmol) was also dried under high vacuum, and dissolved under argon in THF (15 mL). The THF solution was degassed and placed under an argon atmosphere. The solution of thiol was added to the mixture of iodide and $Cs_2CO_3$. The mixture was stirred for 3 h under argon at RT, then degassed DMF (5 mL) was added, and the mixture stirred overnight at RT under argon. The reaction mixture was neutralized with HOAc (3 M) and diluted with $CH_2Cl_2$. The mixture was extracted with saturated $NaHCO_3$ and the aqueous phase re-extracted twice with $CH_2Cl_2$. The combined organic phases were dried over $MgSO_4$, concentrated and dried under high vacuum. The AT dimer was dissolved in THF (20 mL) and MeOH (130 mL). A solution of Oxone (2.21 g; 3.6 mmol) and NaOAc (985 mg; 12 μmol) in $H_2O$ (33 mL) was added for 15 min, and the white suspension stirred for a period of 2 h at RT. The suspension was concentrated to a third of its volume and diluted with saturated $Na_2S_2O_3$ solution. The mixture was extracted three times with $CH_2Cl_2$ and the combined organic phases dried over $MgSO_4$ to yield crude TBDPSO-A$^{Bz}$SO$_2$T-OTBDPS I985 mg, 871 mmol, 105%) of a white foam. A portion was chromatographed to yield an analytical sample ($CH_2Cl_2$:ethyl acetate=8:2 with 0.25% $H_2O$).

$R_f$-value: Intermediate: 0.86; thiol: 0.31($CH_2Cl_2$:ethyl acetate=1:1)

FAB-MS (NOBA matrix): m/z=1156 (14); 1155 (24); 1154 (31); 1135 (11); 1134 (28); 1133 (47); 1132 (M+H$^+$, 62); 1131 (13); 1130 (18); 1076 (17); 1075 (32); 1074 (43); 241 (18); 240 (100); 199 (19); 197 (37); 137 (12); 136 (14); 135 (46); 105 (31)(Only ions with m/z>100 are reported).

UV ($CH_2Cl_2$) $\lambda_{max}$ [nm] ($\epsilon$ in $M^{-1}cm^{-1}$)=273 (25400); 229 (23100).

$^1$H-NMR (DMSO, 300 MHz): δ (ppm)=0.90 (s, 9H, t-Bu); 1.03 (s, 9H, t-Bu); 1.03 (s, 9H, t-Bu); 1.71 (s, 3H, $CH_3$(T)); 1.74–1.86 (m, 2H, H-5'(T)); 2.05–2.16 (m, 1H, H-2'(T)); 2.16–2.23 (m, 1H, H-2'); 2.56 (m, 1H, H-2'(A)); 2.90–2.94 (m, 1H, H-2'(A)); 2.95–3.13 (m, 2H, H6'(T),H-3'(A))); 3.20–3.42 (m, 3H, H-6'(T), 2H-3"(A)); 3.80 (m, 1H, H-5'(A)); 3.93–4.06 (m, 3H, H-5(A), 2H-4'); 4.26 (dd, J=5.2, 2.8, H-3'(T)); 6.26 (t, J=7, 1H, H-1'); 6.47 (dd, J=7.5, 2.6, 1H, H-1'), 7.23–7.66 (m, 24H, 23H arom., H-6(T)); 8.05 (d, J=7.3, 2H, H arom.); 8.58, 8.64 (2s, H-2(A), H-8(A)).

$^{13}$C-NMR ($CDCl_3$, 75 MHz): δ (ppm)=12.29 (q, $CH_3$(T)); 19.04; 19.13 (2s, $C(CH_3)_3$); 25.34 (t, $C_5$(T)); 26.88 (q, $C(CH_3)_3$); 33.89 (d, $C_3$(A)); 38.17, 38.77 (2t, $C_{2'}$); 49.68; 54.46 (2t, $CH_2SO_2CH_2$); 64.29 (t, $C_5$(A)); 75.97 (d, $C_3$(T)); 84.70; 84.82; 85.15; 88.22 (4d, $C_{1'}$, $C_{4''}$); 111.38 (s, $C_5$(T)); 123.27 (s, $C_5$(A)); 127.93; 128.04; 128.11; 128.32; 128.63; 130.07; 130.12; 130.28; 130.39; 132.38; 132.47; 132.63; 132.77; 132.84; 133.68; 135.44; 135.57; 135.66; 137.14 (d, $C_6$(T)); 141.59 (d, $C_6$(T)); 149.89; 150.26 (2s, $C_4$(A), $C_2$(T)); 151.04 (s, $C_6$(A)); 152.72(d, $C_2$(A)); 163.96 (s, $C_4$(T)); 165.12 (s, C=O amide).

HO-A$^{Bz}$SO$_2$T-OH

The protected AT dimer TBDPSO-A$^{Bz}$SO$_2$T-OTBDPS (885 mg; crude) was transferred with $CH_2C_{12}$ to a plastic test tube, concentrated and dried under high vacuum. The residue was dissolved under argon in anhydrous pyridine (2 mL). HF (4.7 M in pyridine; 3 mL; 14 mmol) was added, and the reaction mixture was stirred overnight at RT. An excess of methoxytrimethylsilane (4 mL; 35 mmol) was added and the mixture stirred for 30 min at RT. The solution was transferred into a glass flask and concentrated. The crude product was chromatographed (50 g silica gel; $CH_2Cl_2$:EtOH:MeOH=86:7:7 with 0.25% $H_2O$) to yield HO-A$^{Bz}$SO$_2$T-OH (349 mg, 536 mmol; 68.5%) as a white powder.

FAB-MS (NOBA matrix): m/z (%)=678 (M+Na$^+$) 658 (15); 657 (40); 656 (M+H$^+$, 100); 290 (10); 289 (20); 240 (22) (Only ions with m/z>200 are reported).

UV ($CH_2Cl_2$:MeOH=1:1) λmax [nm] ($\epsilon$ in $M^{-1}cm^{-1}$)= 277 (23900).

$^1$H-NMR (DMSO; 500 MHz): δ=1.79 (d, J=1.0, 3H, $CH_3$(T)); 2.00 (m, 1H, H-5'(T)); 2.07 (ddd, J=13.6, 6.7, 4.1, 1H, H-2'(T)); 2.13 (m, 1H, H-5'(T)); 2.26 (quintet, J=7, 1H, H-2'(T)); 2.57 (ddd, J=13.7, 9.4, 7.3, 1H, H-2'(A)); 2.83 (ddd, J=13.7, 7.8, 2.8, 1H, H-2'(A)); 3.05 (m, 1H, H-3'(A)); 3.22–3.30 (m, 2H, H-6'(T)); 3.38 (dd, J=14.0, 10.1, 1H, H-3"(A)); 3.55 (dd, J=14.0, 3.8, 1H, H-3"(A)); 3.63 (td, J=12,4, 1H, H-5'(A)); 3.73–3.77 (m, 2H, H-5'(A), H-4'(T); 3.92 (td, J=8,4, 1H, H-4'(A);; 4.15 (m, 1H, H-3'(T)); 5.09 (t, J=5.2, 1H, OH (A)); 5.36 (d, J=4.0, 1H, OH (T)); 6.17 (t, J=6.7, 1H, H-1'(T)); 6.45 (dd, J=7.3, 2.8, 1H, H-1'(A)); 7.44

(d, J=1.0, 1H, H-6(T)); 7.54 (m, 2H, H arom.); 7.65 ((m, 1H, H arom.); 8.04 (m, 2H, H arom.); 8.72; 8.73 (2s, H-2(A), H-8(A)); 11.20 (br, 1H, NH); 11.27 (br, 1H, NH).

$^{13}$C-NMR (DMSO, 125 MHz): δ (ppm)=11.96 (q, CH$_3$ (T)); 24.90 (t, C$_5$(T)); 31.94 (d, C$_3$(A)); 37.66; 38.03 (2t, C$_2$'); 49.25 (t, C$_6$(T)); 53.43 (t, C$_{3''}$(A)); 60.72 (t, C$_5$(A)); 72.78 (d, C$_3$(T)); 83.36; 83.74; 84.05; 85.36 (4d, C$_1$'; C4'); 109.90 (s, C$_5$(T)); 125.76 (s, C$_5$(A)); 128.36 (d, CH arom.); 132.31 (d, CH arom.); 133.36 (s, C arom.); 136.09 (d, C$_6$(T)); 142.68 (d, C$_8$(A)); 150.17 (s, C$_4$(A)); 151.31 (d, C$_2$(A)); 151.44 (s, C$_6$(A)); 163.59 (s, C$_4$(T)); 165.58 (s, C=O).

DMTrO-A$^{Bz}$SO$_2$T-OH

HO-A$^{Bz}$SO$_2$T-OH (298 mg; 485 μmol) and DMAP (a few grains) were dried overnight under high vacuum and then dissolved under argon in pyridine (6 mL) and TEA (160 μL; 1.14 mmol). DMTrCl (241 mg; 711 μmol) was added and stirred 3 h at RT. MeOH (1 mL) was added and the pyridine removed under high vacuum. The crude product was chromatographed (50 g silica gel; CH$_2$Cl$_2$:MeOH=98:2; 95:5; 90:10) to yield DMTrO-A$^{Bz}$SO$_2$T-OH (283 mg, 301 mmol, 65.7%) as a white foam.

R$_f$-value: 0.4 (CH$_2$Cl$_2$:MeOH=95:5)

FAB-MS (NOBA matrix): m/z (%)=960 (M+Na$^+$, 24); 959 (58); 958 (M+H$^+$, 100); 304 (21); 303 (58); 289 (10); 240 (30) (Only ions with m/z>200 are reported).

UV (CH$_2$Cl$_2$) λ$_{max}$[nm] (ε in M$^-$cm$^{-1}$)=276 (25100); 236 (31700).

$^1$H-NMR (DMSO, 400 MHz): δ (ppm)=1.76 (d, J=1.1, 3H, CH$_3$(T)); 1.93–2.16 (m, 3H, 2H-5'(T); H-2'); 2.25 (m, 2H, H-2'(T)); 2.58 (m, 1H, H-2'(A)); 3.00 (m, 1H, H-2'(A)); 3.17–3.52 (m, 7H, CH$_2$SO$_2$CH$_2$, H-5'(A),H-3'(A)); 3.70 (2s, 6H, OCH$_3$), 3.73 (m, 1H, H-4'); 4.04 (m, 1H, H-4'); 4.14 (m, 1H, H-3'(T)); 5.35 (d, J=4.5, 1H OH); 6.15 (t, J=7.0, 1H, H-1'); 6.46 (dd, J=7.5, 2.9, 1H, H-1'); 6.79 8m, 4H, H arom.); 7.14–7.23 (m, 7H, H arom.), 7.30 (m, 2H, H arom.); 7.42 (d, J=1.1, 1H, H-6(T)); 7.55 (m, 2H, H arom.); 7.64 (m, 1H, H arom.); 8.04 (m, 2H, H arom.); 8.31; 8.55; 8.69 (2s, H-2(A), H-8(A)).

$^{13}$C-NMR (DMSO, 100 MHz): δ (ppm)=11.95 (q, CH$_3$ (T)); 24.95 (t, C$_5$(T)); 32.95 (d, C$_3$(A)); 36.74; 38.08 (2t, C$_2$'); 49.29 (t, C$_6$(T)); 53.60 (t, C$_{3''}$(A)); 54.86 (q, OCH$_3$), 63.49(t, C$_5$(A)); 72.79 (d, C$_3$'(T)); 79.08; 83.37; 83.71; 84.19 (4d, C$_{1''}$; C$_{4'}$), 85.55 (s, C(ar)$_3$); 109.89 (s, C$_5$(T)); 113.00 (d, CH arom.); 125.84 (s, C arom.); 126.51; 127.54; 127.63; 128.35; 128.38; 129.54; 132.31 (7d, CH arom.); 133.34; 135.36; 135.38 (3s, C arom.); 136.05 (d, C$_6$(T)); 143.04 (d, C$_4$(A)); 151.37 (d, C$_2$(A)); 151.48 (s, C$_6$(A)); 157.93 (s, C arom.,); 163.58 (s, C$_4$(T)); 165.48 (s, C=O Amid).

Preparation of the AT-phosphoramidite

DMTrO-A$^{Bz}$SO$_2$T-OH (100 mg; 1.06 μmol) and DIPAT (9 mg; 52 μmol) were dried under high vacuum at 40° C. for 1 h. The mixture was dissolved under argon atmosphere in CH$_3$CN (0.5 mL). Bis-diisopropylamino-β-cyanoethoxyphosphine (46 mL; 142 μmol) was added and the reaction mixture stirred 3 h at RT. The mixture was then diluted with CH$_2$Cl$_2$ and extracted with saturated NaHCO$_3$ solution. The aqueous phase was re-extracted twice with CH$_2$Cl$_2$, and the combined organic phases dried over MgSO$_4$. The concentrated product was dissolved in CH$_2$Cl$_2$ (2 mL) and precipitated with hexane (20 mL). The suspension was cooled for 30 min to −20° C. and then centrifuged. The supernatant solution was decanted and the white residue dried under high vacuum to yield DMTrO-A$^{Bz}$SO$_2$T-O-phosphoramidite (113 mg, 99 μmol, 94%) as a white foam.

R$_f$-value: 0.26 (petroleum ether:acetone:TEA=4.5:4.5:1)

FAB-MS (NOBA matrix): m/z (%)=1180 (M+Na$^+$, 6); 1176 (12); 1175 (26); 1174 (37); 1161 (11); 1160 (35); 1159 (76); 1158 (M+H$^+$, 100), 304 (36); 303 (96); 240(39); 155 (11); 154 (31); 138 (15); 137 (24); 136 (27); 105 (21); 102 (31) (Only ions with m/z>100 are reported).

$^1$H-NMR (CDCl$_3$, 300 MHz): δ (ppm)=1.18 (d, J=6.5, 12H, (CH$_3$)$_2$CH); 1.87 (d, J=1.2, 1.5H, CH$_3$(T)); 1.88 (d, J=1.3, 1.5H, CH$_3$(T)); 2.10 (m, 1H, H-5'(T)); 2.23–2.42 (m, 3H, H-5'(T), 2H-2'(T)); 2.47–2.78 (m, 4H, 2H-2'(A), CH$_2$CN); 2.95 (m, 1H, H-3'(A)); 3.05–3.27 (m, 4H, CH$_2$SO$_2$CH$_2$); 3.32 (m,1H, H-5'(A)); 3.38–3.51 (m, 2H, H-5'(A), CHOP or CHCN); 3.52–3.89 (m, 3H, CH$_2$OP, CH$_2$CN); 3.76 (s, 6H, OCH$_3$); 3.91–4.09 (m, 2H, H-4'); 4.32 (m, 1H, H-3'(T)); 5.99 (t, J=7.1, 0.5H, H-1'(T)); 6.07 (t, J=6.9, 0.5H, H-1'(T)); 6.43 (d, J=6.5, 1H, H-1'(A)); 6.79 (m, 4H, H arom.); 7.03 (d, J=1.3, 0.5H, H-6(T)); 7.04 (d, J=1.2, 0.5H, H-6(T)); 7.16–7.63 (m, 12H, H arom.); 8.07–8.12 (m, 2H, H arom.); 8.32 (s, 0.5H, H-8(A)); 8.34 (s, 0.5H, H-8 (A)); 8.34 (s, 0.5H, H-8(A)); 8.80 (s, 1H, H-2(A)).

$^{31}$P-NMR (CDCl$_3$, 120 MHz): δ (ppm)=148.94 (s); 149.45 (s).

Example 6

DNA Synthesis

A Gene Assembler Plus of Pharmacia LKB was used for the synthesis of chimeric oligonucleotides. The oligodeoxyribonucleotides were prepared using the βcyanoethyl-N,N-diisopropyl-phosphoramidite method in 1.3 μmol amounts. The phosphoramidite dimers were first dried for 24 h in a desiccator over P$_2$O$_5$. The instructions in the "Gene Assembler Plus Owners Manual" were followed. The oligodeoxynucleotide chimeras were released in the "Trityl-on" form from the support.

Capping A: 3 g DMAP in 50 mL CH$_3$CN

Capping B: 15 mL collidine and 10 mL Ac$_2$O in 25 mL CH$_3$CN

To release the product from the support and to deprotect the nucleobases, the support was transferred with NH4OH (3 mL) to a plastic test tube and incubated 16 h at 55° C. The supernatant was removed by pipette, and the residue washed three times with H$_2$O (1 mL). The combined washing were concentrated on a Speed Vac. The residue was dissolved in 4–5 mL 0.1 M TEAA solution (pH 7) and purified in 3–5 portions by HPLC. The combined fractions were concentrated using a Speed Vac.

To detritylate, the oligonucleotide chimeras were treated with AcOH (500 μL, 80%) for 20 min at RT. The solution was then treated with EtOH (300 μL) and concentrated using a Speed Vac. The residue was dissolved in $H_2O$ (600 μL), and the solution extracted three times with Ether (each 300 μL). The aqueous phase was concentrated using a Speed Vac. The residue was dissolved in $H_2O$ (5 mL) and chromatographed by HPLC in 5 portions. The solvents were again removed by Speed Vac and the residue twice evaporated with $H_2O$ (400 μL, 200 μL) (Speed Vac) to remove residual buffer.

HPLC: Column: LiChrosorb, RP 18, length 25 cm, ⌀=10 mm, particle size 7 μm, L=25 cm. Flow rate: 3 mL/min. UV-Detection at 260 nm molten state divided by the hyperchromicity upon going from 20 to 90° C. Standards were obtained by digestion of the oligonucleotide chimeras and determining the absorbance of the units directly. The digestion was carried out in the same buffer as the melting experiments (0.1 M NaCl; 10 mM $Na_2HPO_4/NaH_2PO_4$; 0.1 mM EDTA; pH 7). To 0.7 mL oligonucleotide solution with A~0.3 was added alkaline Phosphatase (1 μL) and the initial absorbance measured. Phosphodiesterase (Crotalus durissus 1 mL) was added and the increase in absorption followed at RT. After ca. 1 h, the absorption ceased to further increase. The hyperchromicity was the final absorbance divided by the starting absorbance.

TABLE 1

Sequences and Data on some Sulfone-DNA Chimeras

| Seq Id. No. | Sequence | HPLC-Gradient for "Trityl-on"; $t_R$ | HPLC-Gradient for "Trityl-off"; $t_R$ | OD (260nm) $\lambda_{max}$ |
|---|---|---|---|---|
| 3 | 5'GCGTso$_2$TTTGCT3' | Gradient 1; $t_R$ = 35.5 min. | Gradient 3; $t_R$= 42.5 min. | 6.6 260. |
| 3 | 5'GCGTso$_2$TTso$_2$TGCT3' | Gradient 2; $t_R$ = 31.8 min. | Gradient 3; $t_R$= 43.5 min. | 25.3 261 |
| 1 | 5'Tso$_2$TTTTCTAGATCTGGA3' | Gradient 2; $t_R$ = 35.7 min. | Gradient 4; $t_R$= 42.5 min. | 47.8 261 |
| 1 | 5'Tso$_2$TTso$_2$TTCTAGATCTGGA3' | Gradient 2; $t_R$ = 36.0 min. | Gradient 4; $t_R$= 43.5 min. | 53.0 264 |
| 1 | 5'TTTTTCTAGAso$_2$TCTGGA3' | Gradient 2; $t_R$ = 32.5 min. | Gradient 4; $t_R$= 42.5 min. | 36.7 262 |
| 2 | 5'TCCAGAso$_2$TCTAGAAAAA3' | Gradient 2; $t_R$ = 32.0 min. | Gradient 4; $t_R$= 43.0 min. | 42.6 261 |

Gradient 1: Buffer A: 0.1 M TEAA, pH 7, Buffer B: 0.1 M TEAA, pH 7:$CH_3CN$=1:1. Purification is run with buffer A containing 30% of buffer B, increasing to 60% B over a period of 30 min, and then from 60% to 70% B over a period of 10 min.

Gradient 2: Buffer A: 0.1 M TEAA, pH 7. Buffer B: 0.1 M TEAA, pH 7:$CH_3CN$=1:1. Purification is run with buffer A containing 10–20% B in 5 min.; 20–100% B in 40 min.

Gradient 3: Buffer A: 0.1 M TEAA, pH 7. Buffer B: 0.1 M TEAA, pH 7:$CH_3CN$=8:2. Purification is run with buffer A containing 20–40% B over 30 min.; 400–100% B over 10 min.; then to 100% B over 10 min.

Gradient 4: Buffer A: 0.1 M TEAA, pH 7. Buffer B: 0.1 M TEAA, pH 7:$CH_3CN$=8:2. Purification is run with buffer A containing 35% buffer B increasing to 55% B over 30 min.; to 55–100% B over 10 min.; and then to 100% B over 10 min.

Extinction Coefficient ε of an Oligonucleotide Chimera and the Concentration of the Chimera The extinction coefficient of an oligonucleotide in a completely "molten" (unstructured) state is to a good approximation the sum of the extinction coefficients of the monomer units $\epsilon = \Sigma \epsilon_i * n_i(B_i)$ $\epsilon_i$: ε of a Nucleotide; $n_i(B_i)$:number of nucleotide units with Base B;

$\epsilon(dA)$=15400; $\epsilon(dC)$=7300; $\epsilon(dG)$=11700; $\epsilon(T)$=8800

The extinction coefficient of the oligonucleotide at RT is calculated from the extinction coefficient in a completely

TABLE 2

Extinction coefficients and other physical properties of oligonucleotides and their chimeras. A, T, C, and G indicate nucleobases, as in standard oligonucleotides, joined by phosphates. Where the improvement has been made to replace the —O—PO$_2$—O— group by a —CH$_2$—SO$_2$—CH$_2$— group, the position of the improvement is shown by inserting SO$_2$ between the letters indicating the nucleobases.

| SEQ. ID. NO. | Sequence | $\epsilon$[1] | $\epsilon$[2] (nearest neighbor method (20° C.) | A$_{260}$ (20° C.) | A$_{260}$ (° C.) | H | $\epsilon$ korr.[3] (20° C.) | A$_{260}$ before digest (20° C.) | A$_{260}$ after digest (20° C.) | H | $\epsilon$ korr.[4] (20° C.) |
|---|---|---|---|---|---|---|---|---|---|---|---|
| 1 | 5'-TTTCTAGATCTGGA-3' | 166300 | 151200 | 0.2550 | 0.3105 | (96) | 1.22 | 136600 | 0.302 | 0.388 | 1.29 | 128900 |
| 1 | 5'-TTTTTCTAGASO$_2$TCTGGA-3' | 166300 | | 0.2995 | 0.3238 | (96) | 1.08 | 153800 | | | | |
| 1 | 5'-TSO$_2$TTTTCTAGATCTGGA-3' | 166300 | | 0.251 | 0.288 | (92) | 1.15 | 144900 | 0.260 | 0.303 | 1.16 | 142700 |
| 1 | 5'-TSO$_2$TTSO$_2$TTCTAGATCTGGA-3' | 166300 | | 0.314 | 0.365 | (92) | 1.16 | 167700 | | | | |
| 2 | 5'-TCCAGATCTAGAAAAA-3' | 194900 | 169200 | 0.380 | 0.436 | (90) | 1.15 | 169900 | 0.377 | 0.476 | 1.26 | 154700 |
| 2 | 5'-TCCAGASO$_2$TCTAGAAAAA-3' | 194900 | | 0.319 | 0.355 | (92) | 1.11 | 175100 | | | | |
| 3 | 5'-GCGTTTTGCT-3' | 93700 | 85200 | 0.298 | 0.325 | (92) | 1.09 | 85900 | 0.298 | 0.320 | 1.07 | 87300 |
| 3 | 5'-GCGTSO$_2$TTTGCT-3' | 93700 | | 0.292 | 0.318 | (92) | 1.09 | 86000 | | | | |
| 3 | 5'-GCGTSO$_2$TTSO$_2$TGCT-3' | 93700 | | 0.251 | 0.288 | (92) | 1.15 | 81700 | | | | |
| 4 | 5'-AGCAAAACGC-3' | 122300 | 103400 | 0.288 | 0.338 | (92) | 1.17 | 104200 | 0.298 | 0.363 | 1.21 | 100400 |
| 4 | 5'-rAGCAAAACGC-3' | 122300 | 103400 | 0.334 | 0.378 | (92) | 1.13 | 108100 | | | | |

[1] $\epsilon = \Sigma \epsilon_i * n_i(B_i)$, where $\epsilon$ is an extinction coefficient. $\epsilon_1$: $\epsilon$ of a Nucleotides; $n_i(B_i)$: Number of nucleotides with base B; $\epsilon(dA) = 15400$; $\epsilon(dC) = 7300$; $\epsilon(dG) = 11700$; $\epsilon(T) = 8800$
[2] $\epsilon(ABC...XYZ) = 2[\epsilon(AB) + \epsilon(BC) + ...+\epsilon(XY) + \epsilon(YZ)] - (\epsilon B) - (\epsilon C) - ....-\epsilon(X) - \epsilon(Y)$
[3] $\epsilon_{oligo} = \Sigma \epsilon_i * n_i(B_i)/H$; H = Hyperchromicity = A$_{260}$(molten state)/A$_{260}$(20° C.), where A is absorbance.
[4] $\epsilon_{oligo} = \Sigma \epsilon_i * n_i(B_i)/H$; H = A$_{260}$(before digestion)/A$_{260}$ (after digestion)

What is claimed is:

1. An oligonucleotide analog comprising at least one building subunit of the formula

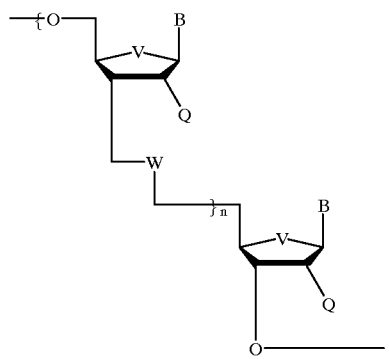

wherein n is an integer less than 25, V is independently selected from —O— or —CH$_2$—, Q is independently selected from the group consisting of —H and —OH, W is independently selected from the group consisting of —S—, —S(O)—, and —S(O$_2$)—, and each B is independently selected from the group consisting of adenine, 7-deazaadenine, 7-deaza-8-azaadenine, 3,7-dideazaadenine, 8-deazaadenine, guanine, 3-deazaguanine, 7-deaza-8-azaguanine, 3,7-dideazaguanine, 3,7-dideaza-8-azaguanine, 7-deazaguanine, 8-azaguanine, purine, azapurine, 2,6-diaminopurine, hypoxanthine, uracil, 5-azauracil, 6-azauracil, 5-fluorouracil, 5-bromouracil, 5-iodouracil, thymine, 6-azathymine, cytosine, 6-azacytosine, 5-azacytosine, pyrimidine, azapyrimidine, pyrrolopyrimidine, pyrazolopyrimidine, triazolopyrimidine, imidazolopyrimidine, pyridine, imidazolopyridine, pyrrolopyridine, pyrazolopyridine, triazolopyridine, and the the structural formulae below, wherein —R designates the point of attachment of the base to position 1 of a ribose or deoxyribose ring, X is either a nitrogen atom or a carbon atom bearing a substituent Z, Z is either a hydrogen, an unfunctionalized lower alkyl chain, or a lower alkyl chain bearing an amino, carboxyl, hydroxy, thiol, aryl, indole, or imidazoyl group, Y is either N or CH, and the ring contains no more than three nitrogens consecutively bonded.

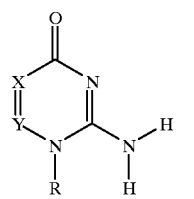
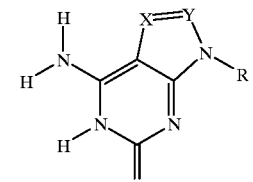

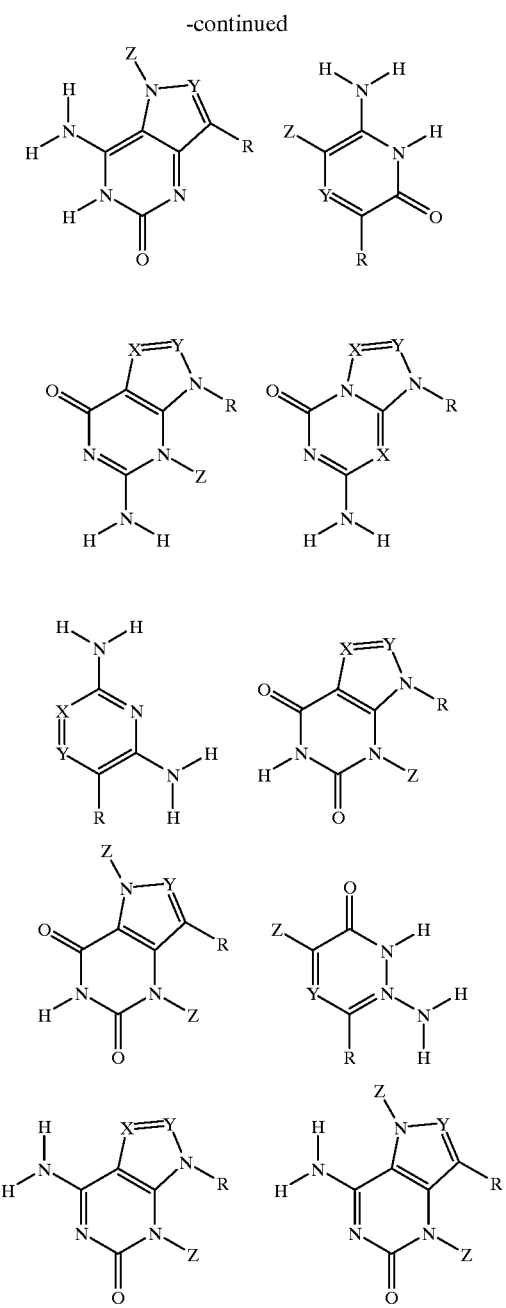

* * * * *